United States Patent [19]

Nitecki et al.

[11] Patent Number: 5,756,066
[45] Date of Patent: May 26, 1998

[54] IODINE-CONTAINING PEPTIDES

[75] Inventors: Danute Nitecki, Berkeley, Calif.; Werner Krause, Berlin, Germany; Franz-Karl Maier, Berlin, Germany; Gabriele Schuhmann-Giampieri, Berlin, Germany; Wolf-Rudiger Press, Berlin, Germany; Peter Muschick, Ladenburg, Germany; Sara Biancalana, Corte Madera, Calif.

[73] Assignee: Schering Aktiengesellschaft, Berlin, Germany

[21] Appl. No.: 487,096

[22] Filed: Jun. 7, 1995

[51] Int. Cl.$^6$ .................. A61K 51/00; A61M 36/14
[52] U.S. Cl. .................. 424/1.69; 424/1.65; 424/9.4; 424/9.45; 424/1.85; 530/300
[58] Field of Search ............... 424/1.11, 1.65, 424/1.69, 1.85, 9.1, 9.3, 9.4, 9.43, 9.44, 9.45, 9.455, 9.5; 530/300, 324–330

[56] References Cited

U.S. PATENT DOCUMENTS 5,229,490 7/1993 Tam .............................. 530/324

FOREIGN PATENT DOCUMENTS

| 0 206 551 | 12/1986 | European Pat. Off. |
| 0 436 316 | 7/1991 | European Pat. Off. |
| 88/06162 | 8/1988 | WIPO |
| 93/10824 | 6/1993 | WIPO |

*Primary Examiner*—John Kight
*Assistant Examiner*—Dameron Jones
*Attorney, Agent, or Firm*—Millen, White, Zelano, & Branigan, P.C.

[57] ABSTRACT

Iodine-containing peptides of general formula I

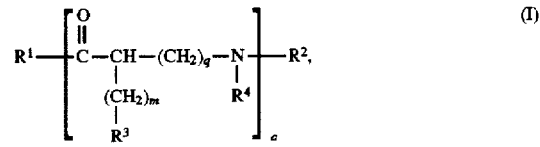

in which $R^1$, $R^2$, $R^3$, $R^4$, a, m and q have the meanings indicated in the description, agents containing these compounds, the use of compounds as contrast media as well as processes for their production are described.

28 Claims, 1 Drawing Sheet

IODINE-CONTAINING PEPTIDES

SUMMARY OF THE INVENTION

The invention relates to iodine-containing peptides, agents containing these compounds, the use of the compounds as contrast media as well as processes for their production.

X-ray contrast media are indispensable auxiliary agents in the diagnosis of numerous diseases, such as, e.g., of arteriosclerotic vascular processes, tumors, infarcts, diseases of the kidneys and efferent urinary passages and perfusion disorders, e.g., in the heart (ischemia, as well as inflammations).

The requirements that are to be placed on such contrast media above all relate to a) a sufficiently high iodine concentration of the solution used. As long as the agent is not diluted, the iodine concentration is the sole parameter upon which X-ray opacity of the contrast medium depends. This is especially the case in angiography if the contrast medium is injected at high speed by catheter into blood vessels and thus displaces the blood.

In a number of other studies, highly concentrated contrast media are also desired, e.g., if the dilution in the body otherwise becomes too great (injection in the ventricles of the heart, the aorta or in intravenous digital subtraction angiography) or in the case of unfavorable radiographic conditions (for example, the path of rays through the body of a heavy patient can be very long);

b) the chemotoxicity, an inherent property of the contrast medium solutions, which, among others, is linked with the lipophilia of the molecules, their protein-affinity and electron density. It manifests itself in clinical use by the occurrence of side effects, such as nausea, vomiting, certain reactions of the circulatory system, hives, bronchiospasm and other symptoms up to shock and death. Chemotoxic effects can be measured pharmacologically, e.g., as $LD_{50}$ after intravenous injection in animals;

c) the viscosity, a value, which is important for the process of administration of the contrast media, e.g., if larger volumes (30–100 ml) of highly-concentrated and thus more highly-viscous solutions are to be injected quickly. In addition to the poor injectability, more highly viscous contrast media also have the drawback of poor miscibility with blood (formation of streaks instead of homogeneous filling of the cavities of the heart or blood vessels) and the obstruction of the passage through capillaries, e.g., of the lungs;

d) the osmolality of the contrast media-solutions. In the case of the administration of solutions that are strongly hypertonic relative to the blood and tissues (the physiological value is 310 m osm/kg), water exits from the cells, by which, i.a., cell membranes are destroyed and the entire electrolyte metabolism is disturbed. As a result, a large number of side effects, some of them serious, such as, e.g., drop in blood pressure, bradycardia up to cardiac arrest, disorders of the blood-brain barrier, angialgias, etc., are caused;

e) a solubility, which must be sufficiently high for the practical use of the contrast media at physiological pH values in water, but without simultaneously too greatly impairing compatibility and iodine content of the molecule;

f) a chemical stability of the contrast media solutions, which allows a heat-sterilization, and produces a shelf life (storability) of at least 24 months.

Polymeric X-ray contrast media can, in principle, be used enterally or parenterally.

For the visualization of vessels, X-ray contrast media would be desirable that are spread exclusively in the vascular space, i.e., the distribution volume of the contrast medium should be analogous to the intravascular space. The contrast media so far used for angiography are subject to the drawback that they leave the vascular space very quickly, since they are too small and hydrophilic and can spread in the extracellular space. Moreover, their elimination takes place so quickly that generally a local application must be performed by catheter (e.g., in the cranial area) —subject the patient to much discomfort. Accordingly, blood-pool agents (perfusion agents), which make it possible to differentiate tissue well supplied with blood from tissue with insufficient blood supply after systemic administration with the help of X-ray technology, would be desirable for diagnosing an ischemia. Also, if a vascular contrast medium is used, it would be possible to differentiate infarcted tissue, based on its anemia, from the surrounding healthy or ischemic tissue. This is of special importance if, e.g., an object of the diagnostic procedure is to distinguish a cardiac infarction from an ischemia.

Another possible use involves the diagnosis of vascular areas with reduced or increased permeability, which can be caused, e.g., by inflammations or by tumors, as well as use in lymphography and mammography.

Therefore, there exists a need for X-ray contrast media that can mark the vascular space (blood-pool agents). These compounds are to be distinguished by a good compatibility as well as by a high effectiveness (high increase of the signal intensity or reduction of the dose) and by the molecules remaining in the vascular space (no extravasation) as well as by a longer half-life in comparison to the contrast media used for the angiography.

The attempt to solve at least a part of these problems by using iodized macromolecular contrast media so far has been successful only to a very limited extent.

Thus, the dextran derivatives described in international patent application WO 88/06162 exhibit a broad molecular weight distribution and, associated therewith, an incomplete elimination and insufficient compatibility.

The iodine-containing polyamines disclosed in international patent application WO 93/10824 are not very well soluble in water and, moreover, are relatively poorly compatible.

An object of this invention is to provide new X-ray contrast media, particularly for detecting and localizing vascular diseases, which do not have the above-mentioned drawbacks.

Upon further study of the specification and appended claims, further objects and advantages of this invention will become apparent to those skilled in the art.

It has now been found that iodine-containing peptides of general formula I

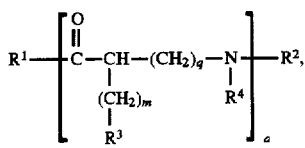 (I)

in which

R¹ stands for the group —OR⁵ or

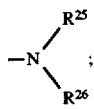

R² stands for a dendrimere having $$\sum_{k=0}^{n-1} 2^k$$

reproduction units R, n represents the number of generations and is 1–100, q is 0–6, R is a radical of formula II

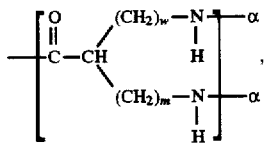 (II)

wherein

α for each generation up to n−1 is, in each case, a reproduction unit R, and for the nth generation is, in each case, the group

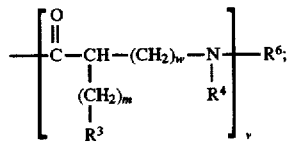

wherein v is 1–100;

R³ stands for a hydrogen atom, hydroxy, phenyl, straight-chain or branched $C_1$–$C_6$ alkyl optionally substituted by hydroxy, or a group

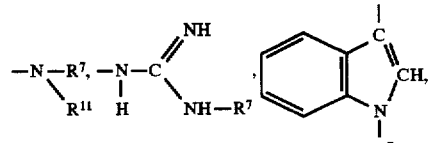

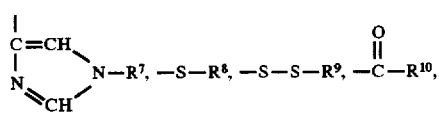

or

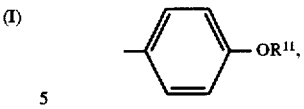

and

R⁴ stands for a hydrogen atom, $C_1$–$C_4$ alkyl or $C_1$–$C_8$ acyl optionally monosubstituted or polysubstituted by hydroxy, or the group —$(CH_2)_n$—COOH or

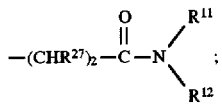

R³ and R⁴ can alternatively together with the nitrogen atom form a 5- or 6-membered ring, wherein each R³ group can be the same or different and each R⁴ group can be the same or different;

R⁵ stands for a hydrogen atom, a saccharide, an oligosaccharide, or a polysaccharide;

or if q in each case is 0,

R³ in each case can also be either —NR¹¹—CO— or —S—S— connected to a further backbone of the formula

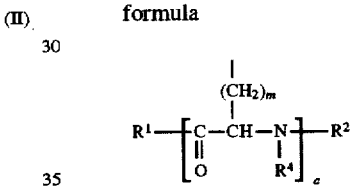

to yield a dimer structure of the formula

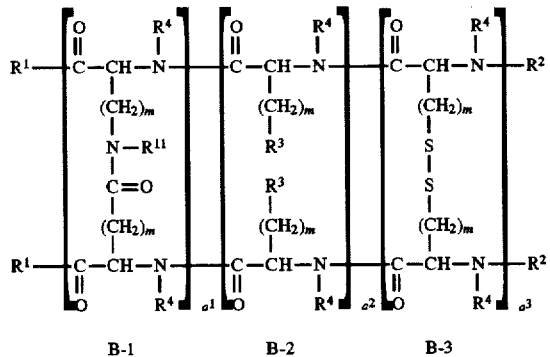

wherein $a^1$, $a^2$ and $a^3$, in each case, is 0–200, $a^1+a^2+a^3=a$, the individual B-1, B-2 and B-3 units can be in any order, and each of the B-1, B-2 and B-3 units can be the same or different;

R⁶ and R⁷, independently in each case, stand for the group

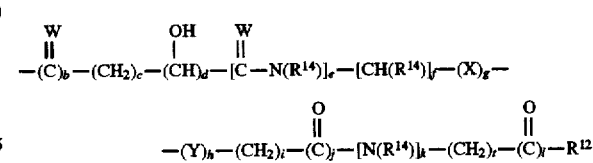

or the group

or the group

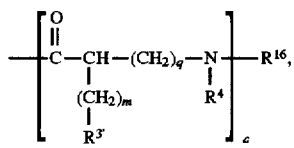

X stands for an oxygen or sulfur atom or the group

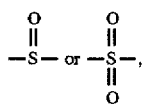

Y stands for the group

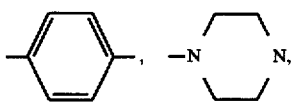

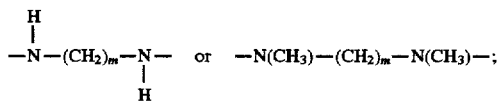

W stands for an oxygen or sulfur atom.

$R^8$ stands for a hydrogen atom, $C_1$–C6 alkyl or $C_1$–$C_{10}$ acyl.

$R^9$ means the group

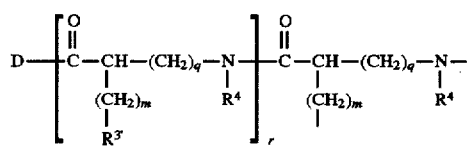

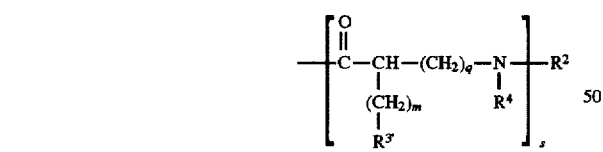

$R^{10}$ means hydroxy or the group

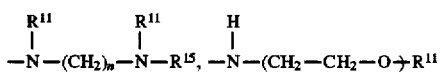

or

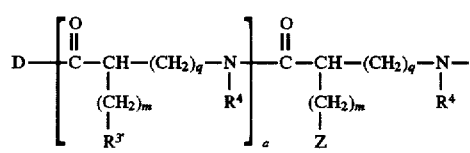

D means hydroxy or the group

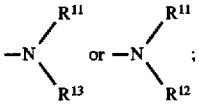

Z means the group

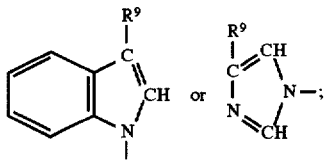

$R^{11}$ stands for a hydrogen atom, $C_1$–$C_4$ alkyl optionally mono- or polysubstituted by hydroxy, or the group —$(CH_2)_n$—COOH.

$R^{12}$ stands for a hydrogen atom or hydroxy or the group

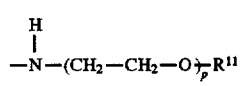

or an iodized benzene ring of the formula

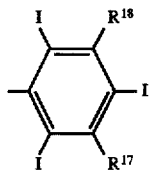

$R^{13}$ stands for the group

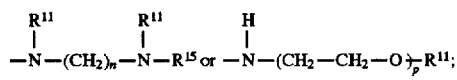

$R1^4$ stands for a hydrogen atom, a carboxy group or a $C_1$–$C_{20}$ alkyl optionally interrupted one or more times by an oxygen atom and/or mono- or polysubstituted by a hydroxy, carboxy, sulfono, phosphono and/or $C_1$–$C_3$ alkoxy group, or the group

$R^{15}$ has the meaning mentioned under $R^6$ and $R^7$.
$R^{16}$ stands for the group

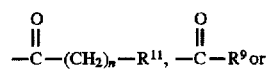

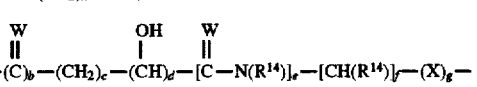

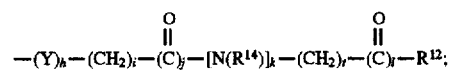

$R^{17}$ and $R^{18}$, respectively independently of one another, stand for a hydrogen atom or a group —$CONR^{20}R^{21}$ or —$NR^{22}COR^{23}$ $R^{19}$ means a $C_1$–$C_4$ alkyl optionally interrupted one or more times by an oxygen atom and/or optionally mono- or polysubstituted by a hydroxy, carboxy, sulfono, phosphono and/or $C_1$–$C_3$ alkoxy group, $R^{20}$ and $R^{21}$, independently of one another, stand for a hydrogen atom, a $C_1$–$C_{12}$ alkyl, $C_3$–$C_{12}$ cycloalkyl, $C_3$–$C_{12}$ cycloalkyl-$C_{1-12}$ alkyl, or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a hydroxy, $C_1$–$C_3$ alkoxy, carboxy, sulfo and/or phosphono group, or $R^{20}$ and $R^{21}$ alternatively can together with the nitrogen atom form a 5- or 6-membered ring, which optionally can contain an oxygen atom or the group

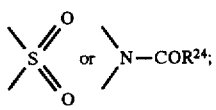

$R^{22}$ stands for a hydrogen atom or a $C_1$–$C_{12}$ alkyl, $C_3$–$C_{12}$ cycloalkyl, $C_3$–$C_{12}$ cycloalkyl-$C_{1-12}$ alkyl, or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a carboxy, sulfono, phosphono group and/or hydroxy group, $R^{23}$ stands for a carboxy group or a straight chain or branched chain $C_1$–$C_{12}$ alkyl, which is optionally interrupted one or more times by an oxygen atom, a carbonyl group and/or an imino group wherein the latter is optionally substituted by a carboxymethyl group, and/or the $C_{1-12}$-alkyl is optionally mono- or polysubstituted by a hydroxy, carboxy, sulfono, phosphono and/or $C_1$–$C_3$ alkoxy group, and $R^{24}$ stands for a carboxy group or a $C_1$–$C_{12}$ alkyl optionally interrupted one or more times by a carbonyl group and/or optionally mono- or polysubstituted by a hydroxy, $C_1$–$C_3$ alkoxy, carboxy, sulfono or phosphono group, $R^{25}$ and $R^{26}$ are the same or different and stand for $C_1$–$C_{20}$ alkyl optionally interrupted by one or more nitrogen or oxygen atoms, and the nitrogen atoms can be substituted by a hydrogen atom or by the group

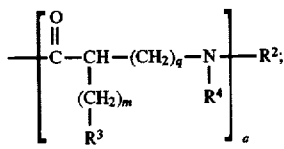

$R^{27}$ stands for a hydrogen atom or $C_1$–$C_4$ alkyl, $R^{3'}$ stands for a hydrogen atom, hydroxy, phenyl, $NR_2'^{11}$ straight-chain or branched alkyl optionally substituted by hydroxy, or $R^{3'}$ and $R^4$ can together with the nitrogen atom form a 5- or 6-membered ring, a in each case stands for 0–200, b, e, g, h, j, k and l are, in each case, the same or different and stand for 0 or 1, c and i are, in each case, the same or different and stand for 0 to 10, d, f, m, p, t and w are, in each case, the same or different and stand for 0 to 6, n stands for 0 to 20, and r and s are, in each case, the same or different and stand for 0 to 100, wherein the total sum of all subscripts a, r, s and v is 10–200, and wherein at least 10 iodized benzene radicals are contained in the peptide; and their salts with physiologically acceptable organic and inorganic bases, amino acids and amino acid amides exhibit better properties relative to the known compounds.

Preferred iodine-containing peptides are the compounds of general formula I, in which $R^1$ stands for hydroxy, $R^2$ stands for a dendrimere having $$\sum_{k=0}^{n-1} 2^k$$

reproduction units R, n represents the number of generations and is 10 1–100, q is 0–6, e.g., 1–6, R is a radical of formula II

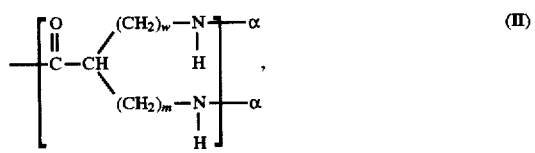

wherein

α for each generation up to n–1 is, in each case, a reproduction unit R, and for the nth generation is, in each case, the group

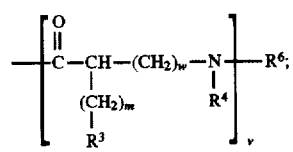

wherein v is 1–100;

$R^3$ stands for a hydrogen atom, hydroxy, phenyl, straight-chain or branched $C_1$–$C_6$ alkyl, optionally substituted by hydroxy, or a group

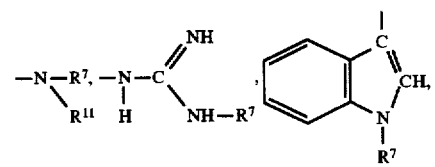

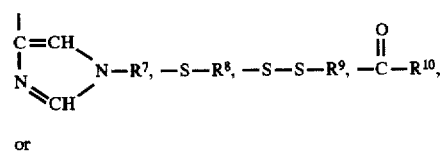

or

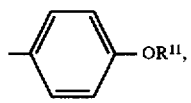

and

R$^4$ stands for a hydrogen atom, C$_1$–C$_4$ alkyl or C$_1$–C$_8$ acyl optionally mono- or polysubstituted by hydroxy, or the group —(CH$_2$)$_n$—COOH or

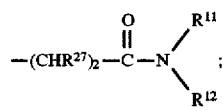

R$^3$ and R$^4$ alternatively can together with the nitrogen atom form a 5- or 6-membered ring, wherein each R$^3$ group can be the same or different and each R$^4$ group can be the same or different; and R$^6$ and R$^7$ independently stand for the group

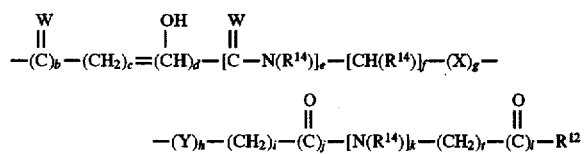

or the group

or the group

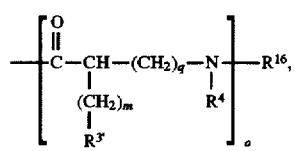

X stands for an oxygen or sulfur atom or the group

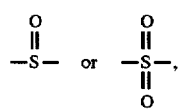

Y stands for the group

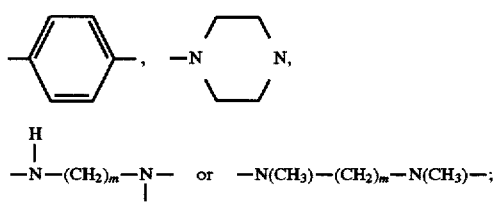

W stands for an oxygen or sulfur atom,

R$^8$ stands for a hydrogen atom, C$_1$–C$_6$ alkyl or C$_1$–C$_{10}$ acyl,

R9 means the group

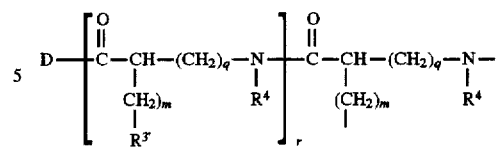

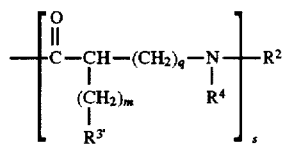

R$^{10}$ means hydroxy or the group

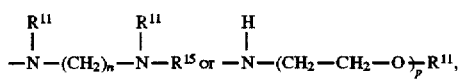

D means hydroxy or the group

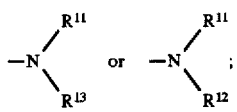

R$^1$ stands for a hydrogen atom, C$_1$–C$_4$ alkyl optionally mono- or polysubstituted by hydroxy, or the group —(CH$_2$)$_n$—COOH.

R$^{12}$ stands for a hydrogen atom or hydroxy or the group

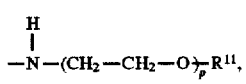

or an iodized benzene ring

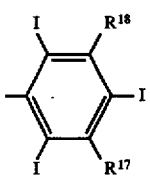

R$^{13}$ stands for the group

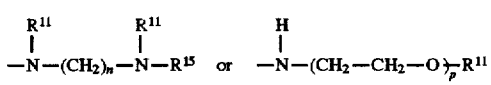

R$^{14}$ stands for a hydrogen atom, a carboxy group or a C$_1$–C$_{20}$ alkyl optionally interrupted one or more times by an oxygen atom and/or optionally mono- or polysubstituted by a hydroxy, carboxy, sulfono, phosphono and/or C$_1$–C$_3$ alkoxy group, or the group

R$^{15}$ has the meaning mentioned under R$^6$ and R$^7$, $R^{16}$ stands for the group $$-\overset{O}{\underset{\|}{C}}-(CH_2)_n-R^{11},\ -\overset{O}{\underset{\|}{C}}-R^9\text{ or}$$

$$-(C)_b-(CH_2)_c-(CH)_d-\overset{W}{\underset{\|}{|}}\overset{OH}{\underset{|}{|}}\overset{W}{\underset{\|}{|}}-(X)_g-$$

$$-(Y)_h-(CH_2)_i-(C)_j-[N(R^{14})]_k-(CH_2)_f-(C)_f-R^{12};$$

$R^{17}$ and $R^{18}$, respectively independently of one another, stand for a hydrogen atom or a group —$CONR^{20}R^{21}$ or —$NR^{22}COR^{23}$ $R^{19}$ means a $C_1$-$C_4$ alkyl optionally interrupted one or more times by an oxygen atom and/or optionally mono- or polysubstituted by a hydroxy, carboxy, sulfono, phosphono and/or $C_1$-$C_3$ alkoxy group, $R^{20}$ and $R^{21}$, independently of one another, stand for a hydrogen atom, a $C_1$-$C_{12}$ alkyl, $C_3$-$C_{12}$ cycloalkyl, $C_3$-$C_{12}$ cycloalkyl-$C_{1-12}$ alkyl or $C_3$-$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a hydroxy, $C_1$-$C_3$ alkoxy, carboxy, sulfo and/or phosphono group, or $R^{20}$ and $R^{21}$ alternatively can together with the nitrogen atom form a 5- or 6-membered ring, which optionally can contain an oxygen atom or the group $$\overset{O}{\underset{\diagdown}{\diagup}}\overset{\diagup}{\underset{\diagdown}{S}}\overset{\diagdown}{\underset{\diagup}{}} \text{ or } \diagdown N-COR^{24};$$

$R^{22}$ stands for a hydrogen atom or a $C_1$-$C_{12}$ alkyl, $C_3$-$C_{12}$ cycloalkyl, $C_3$-$C_{12}$ cycloalkyl-$C_{1-12}$ alkyl or $C_3$-$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a carboxy, sulfono, phosphono group and/or hydroxy group, $R^{23}$ stands for a carboxy group or a straight chain or branched chain $C_1$-$C_{12}$ alkyl which is optionally interrupted one or more times by an oxygen atom, a carbonyl group and/or an imino group wherein the latter is optionally substituted by a carboxymethyl group, and/or the $C_{1-12}$-alkyl is optionally mono- or polysubstituted by a hydroxy, carboxy, sulfono, phosphono and/or $C_1$-$C_3$ alkoxy group, and $R^{24}$ stands for a carboxy group or a $C_1$-$C_{12}$ alkyl optionally interrupted one or more times by a carbonyl group and/or optionally mono- or polysubstituted by a hydroxy, $C_1$-$C_3$ alkoxy, carboxy, sulfono or phosphono group, $R^{27}$ stands for a hydrogen atom or $C_{1-C4}$ alkyl, $R^{3'}$ stands for a hydrogen atom, hydroxy, phenyl, $NR_2^{11}$ straight-chain or branched alkyl optionally substituted by hydroxy, or $R^{3'}$ and $R^4$ can together with the nitrogen atom form a 5- or 6-membered ring, a in each case stands for 0–2003, b, e, g, h, j, k and l are, in each case, the same or different and stand for 0 or 1, c and i are, in each case, the same or different and stand for 0 to 10, d, f, m, p, t and w are, in each case, the same or different and stand for 0 to 6, n stands for 0 to 20, and r and s are the same or different and stand for 0 to 100, wherein the total sum of all subscripts a, r, s and v is 10–200, and wherein at least 10 iodized benzene radicals are contained in the peptide; and their salts with physiologically acceptable organic and inorganic bases, amino acids and amino acid amides.

Especially preferred iodine-containing peptides are the compounds of general formula I, in which $R^1$ stands for hydroxy, $R^2$ stands for a dendrimere having $$\sum_{k=0}^{n-1} 2^k$$

reproduction units R, n represents the number of generations and is 1–100, q is 0–6, e.g., 1–6, R is a radical of formula II $$\left[ \overset{O}{\underset{\|}{C}}-CH\diagup\diagdown\overset{(CH_2)_w-N-}{\underset{H}{|}}\alpha \atop \overset{(CH_2)_m-N-}{\underset{H}{|}}\alpha \right] \quad (II)$$

wherein

α for each generation up to n−1 is, in each case, a reproduction unit R, and for the nth generation is, in each case, the group $$\left[ \overset{O}{\underset{\|}{C}}-CH-(CH_2)_w-N-R^6 \atop \overset{(CH_2)_m}{\underset{R^3}{|}} \quad R^4 \right]_v,$$

wherein v is 1–100, $R^3$ stands for a hydrogen atom, phenyl, straight-chain or branched $C_1$-$C_6$ alkyl or a group $$-N-R^7, \quad \underset{R^{11}}{\diagup}\text{(benzimidazolyl)}\diagdown CH_2, \quad \underset{N}{\overset{C=CH}{\diagdown}}N-R^7, \atop \overset{N}{\underset{R^7}{|}} \quad \diagup\overset{\|}{CH}$$

$$-S-R^8, \quad -S-S-R^9, \text{ or } -\overset{O}{\underset{\|}{C}}-R^{10},$$

and $R^4$ stands for a hydrogen atom, methyl or ethyl, $R^3$ and $R^4$ alternatively can together with the nitrogen atom form a 5- or 6-membered ring, wherein each $R^3$ group can be the same or different and each $R^4$ group can be the same or different; and $R^6$ and $R^7$ stand for the group $$-\overset{O}{\overset{\|}{C}}-R^{12},\quad -\overset{O}{\overset{\|}{C}}-\overset{H}{\overset{|}{N}}-R^{12},\quad -\overset{S}{\overset{\|}{C}}-\overset{H}{\overset{|}{N}}-R^{12},$$

$$-\overset{O}{\overset{\|}{C}}-CH_2-\overset{R^{11}}{\overset{|}{N}}-CH-COOH,$$

$$-\overset{O}{\overset{\|}{C}}-CH_2-O-CH_2-\overset{O}{\overset{\|}{C}}-OH,$$

$$-\overset{O}{\overset{\|}{C}}-CH_2-N(CH_2CO_2H)-\overset{O}{\overset{\|}{C}}-R^{12},$$

$$-\overset{O}{\overset{\|}{C}}-(CH_2)_n-\overset{O}{\overset{\|}{C}}-\overset{R^{11}}{\overset{|}{N}}-R^{12},\quad -(CHR^{27})_2-\overset{O}{\overset{\|}{C}}-\overset{|}{\underset{R^{12}}{N}}-R^{11},$$

$$-\overset{O}{\overset{\|}{C}}-(CH_2)_n-R^{11},\quad -\overset{O}{\overset{\|}{C}}-\overset{OH}{\overset{|}{CH}}-\overset{OH}{\overset{|}{CH}}-\overset{R^{11}}{\overset{|}{N}}-R^{12}\text{ or}$$

$$-\overset{O}{\overset{\|}{C}}-R^9$$

or the group $$\left[\overset{O}{\overset{\|}{C}}-\underset{\underset{R^{3'}}{|}}{\overset{|}{\underset{(CH_2)_m}{CH}}}-(CH_2)_q-\underset{\overset{|}{R^4}}{N}\right]_q R^{16}$$

bound by the C-terminal end;

$R^8$ stands for a hydrogen atom or $C_1$–$C_6$ alkyl, $R^9$ means the group $$D\!-\!\!\left[\overset{O}{\overset{\|}{C}}-\underset{\underset{R^{3'}}{|}}{\overset{|}{\underset{(CH_2)_m}{CH}}}-(CH_2)_q-\underset{\overset{|}{R^4}}{N}\right]_r\!\!\left[\overset{O}{\overset{\|}{C}}-\underset{\underset{R^{3'}}{|}}{\overset{|}{\underset{(CH_2)_m}{CH}}}-(CH_2)_q-\underset{\overset{|}{R^4}}{N}-\right]$$

$$\left[\overset{O}{\overset{\|}{C}}-\underset{\underset{R^{3'}}{|}}{\overset{|}{\underset{(CH_2)_m}{CH}}}-(CH_2)_q-\underset{\overset{|}{R^4}}{N}\right]_s R^2$$

$R^{10}$ means hydroxy or the group $$-\overset{R^{11}}{\overset{|}{N}}-(CH_2)_n-\overset{R^{11}}{\overset{|}{N}}-R^{15}\text{ or }-\overset{H}{\overset{|}{N}}-(CH_2-CH_2-O)_p R^{11},$$

D means hydroxy or the group $$-N\!\!\begin{array}{c}R^{11}\\ \diagup \\ \diagdown\\ R^{13}\end{array}\text{ or }-N\!\!\begin{array}{c}R^{11}\\ \diagup \\ \diagdown\\ R^{12}\end{array};$$

$R^{11}$ stands for a hydrogen atom, $C_1$–$C_4$ alkyl optionally mono- or polysubstituted by hydroxy, or the group $-(CH_2)_n-COOH$, $R^{12}$ stands for an iodized benzene ring $$\begin{array}{c}I\quad R^{18}\\ \diagup\!\!\diagdown\\ |\quad\quad|-I\\ \diagdown\!\!\diagup\\ I\quad R^{17}\end{array}$$

$R^{13}$ stands for the group $$-\overset{R^{11}}{\overset{|}{N}}-(CH_2)_n-\overset{R^{11}}{\overset{|}{N}}-R^{15}\text{ or }-\overset{H}{\overset{|}{N}}-(CH_2-CH_2-O)_p R^{11};$$

$R^{15}$ has the meaning indicated under $R^6$ and $R^7$.

$R^{16}$ stands for the group $$-\overset{O}{\overset{\|}{C}}-R^{12},\quad -\overset{O}{\overset{\|}{C}}-\overset{H}{\overset{|}{N}}-R^{12},\quad -\overset{S}{\overset{\|}{C}}-\overset{H}{\overset{|}{N}}-R^{12},$$

$$-\overset{O}{\overset{\|}{C}}-CH_2-\overset{R^{11}}{\overset{|}{N}}-CH-COOH,$$

$$-\overset{O}{\overset{\|}{C}}-CH_2-O-CH_2-\overset{O}{\overset{\|}{C}}-OH,$$

$$-\overset{O}{\overset{\|}{C}}-CH_2-N(CH_2CO_2H)-\overset{O}{\overset{\|}{C}}-R^{12},$$

$$-\overset{O}{\overset{\|}{C}}-(CH_2)_n-\overset{O}{\overset{\|}{C}}-\overset{R^{11}}{\overset{|}{N}}-R^{12},\quad -(CHR^{27})_2-\overset{O}{\overset{\|}{C}}-\overset{|}{\underset{R^{12}}{N}}-R^{11},$$

$$-\overset{O}{\overset{\|}{C}}-(CH_2)_n-R^{11},\quad -\overset{O}{\overset{\|}{C}}-\overset{OH}{\overset{|}{CH}}-\overset{OH}{\overset{|}{CH}}-\overset{R^{11}}{\overset{|}{N}}-R^{12}\text{ or}$$

$$-\overset{O}{\overset{\|}{C}}-R^9,$$

$R^{17}$ and $R^{18}$, respectively independently of one another, stand for a hydrogen atom or a group $-CONR^{20}R^{21}$ or $-NR^{22}COR^{23}$ $R^{20}$ and $R^{21}$, independently of one another, stand for a hydrogen atom, a $C_1$–$C_{12}$ alkyl, $C_3$–$C_{12}$ cycloalkyl, $C_3$–$C_{12}$ cycloalkyl-$C_{1-12}$ alkyl, or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a hydroxy, $C_1$–$C_3$ alkoxy, carboxy, sulfo and/or phosphono group, or $R^{20}$ and $R^{21}$ alternatively can together with the nitrogen atom form a 5- or 6-membered ring, which optionally can contain an oxygen atom or the group $$\begin{array}{c}\diagdown\quad\diagup\!\!^O\\ \phantom{x}S\\ \diagup\quad\diagdown\!\!_O\end{array}\text{ or }\begin{array}{c}\diagdown\\ N-COR^{24};\\ \diagup\end{array}$$

$R^{22}$ stands for a hydrogen atom or a $C_1$–$C_{12}$ alkyl, $C_3$–$C_{12}$ cycloalkyl, $C_3$–$C_{12}$ cycloalkyl-$C_{1-12}$ alkyl, or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a carboxy, sulfono, phosphono group and/or hydroxy group, $R^{23}$ stands for a carboxy group or a straight chain or branched chain $C_1$–$C_{12}$ alkyl which is optionally interrupted one or more times by an oxygen atom, a carbonyl group and/or an imino group wherein the latter is optionally substituted by a carboxymethyl group, and/or the $C_{1-12}$-alkyl is optionally mono- or polysubstituted by a hydroxy, carboxy, sulfono, phosphono and/or $C_1$–$C_3$ alkoxy group, and $R^{24}$ stands for a carboxy group or a $C_1$–$C_{12}$ alkyl optionally interrupted one or more times by a carbonyl group and/or optionally mono- or polysubstituted by a hydroxy, $C_1$–$C_3$ alkoxy, carboxy, sulfono or phosphono group, $R^{27}$ stands for a hydrogen atom or $C_1$–$C_4$ alkyl, $R^{3'}$ stands for a hydrogen atom, hydroxy, phenyl, $NR_2^{,11}$ straight-chain or branched alkyl optionally substituted by hydroxy, or $R^{3'}$ and $R^4$ can together with the nitrogen atom form a 5- or 6-membered ring, a in each case stands for 0–200, m stands for 0 to 4, p is, in e ach case, the same or different and stands for 0 to 6, n stands for 0 to 20 and r and s are, in each case, the same or d ifferent and stand for 0 to 100, wherein the total sum of all subscripts a, r, s and v is 10–200, and wherein at least 10 iodized benzene radicals are contained in the peptide, as well as their salts with physiologically harmless organic and inorganic bases, amino acid s an d amino acid amides.

The peptides according to the invention exhibit a molecular weight of about 5,000–5,000,000, preferably 10,000–500,000, especially 20,000–100,000.

The iodine-containing peptides generally contain at least 10 and at most 200 radicals of the subformula

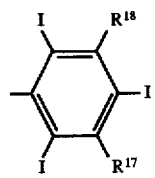

The iodine-containing peptides can also contain a saccharide, such as, e.g., saccharose, or an oligosaccharide, or polysaccharide, such as, e.g., amylose or amylopectin, in the position of $R^5$ instead of a hydrogen atom.

The sum of subscripts a, r, s and v, which indicates the general number of amino acids in the peptide, is generally 10–200, preferably 20–100, e.g., 20–80, and especially preferably 30–80, e.g., 30–60.

Thus, the compounds of general formula I contain up to 200 amino acid groups of the following subformula lined up next to one another

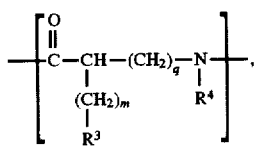

which can optionally be linked with one another, i.e., for example, compounds of the structure:

α-linkage:

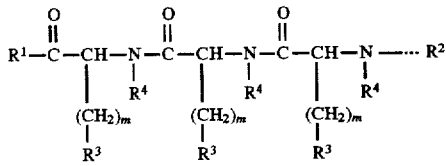

Other linkage possibilities:

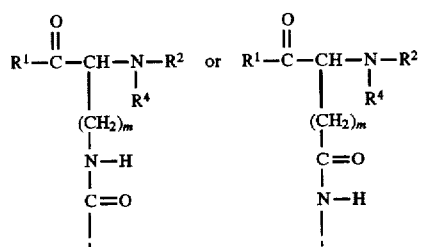

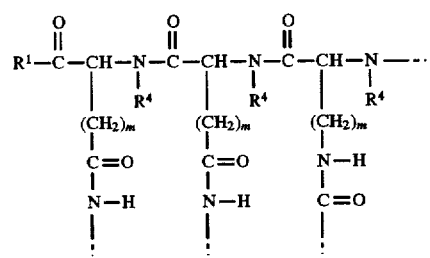

or

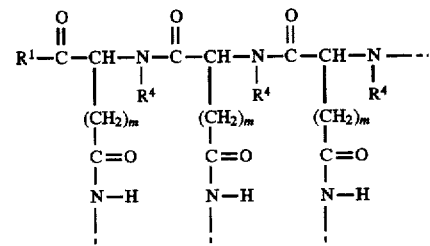

For example, the "peptide backbone" and the iodine-containing peptide can be constituted as follows (the following formulae are shown in conventional amino to carbonyl nomenclature):

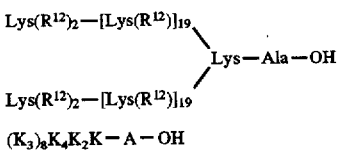

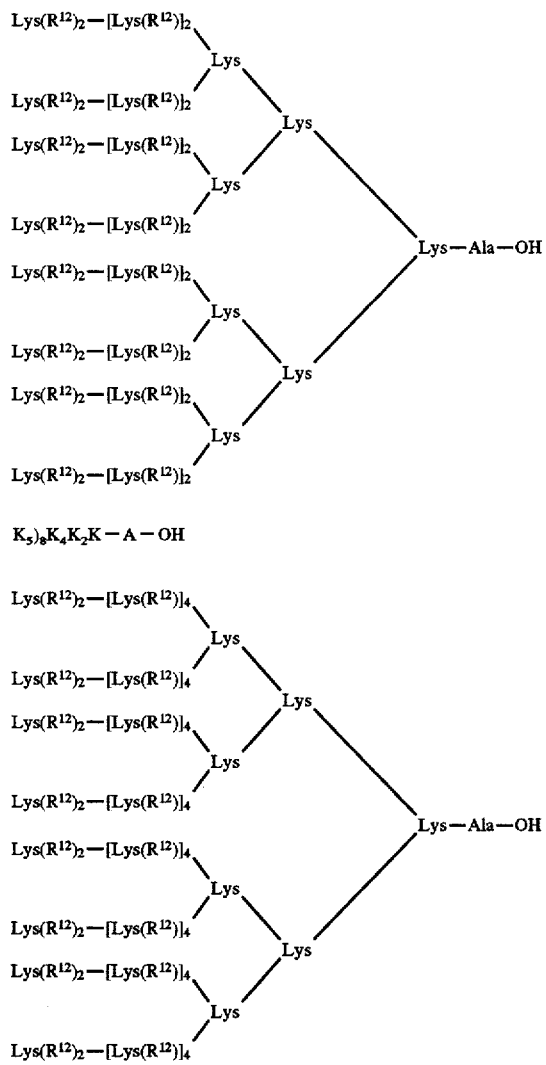

K, Lys=lysyl radical; A, Ala=alanyl radical. Also, a branching or dimerization of the form

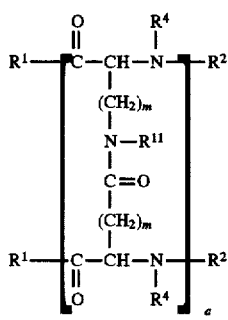

or

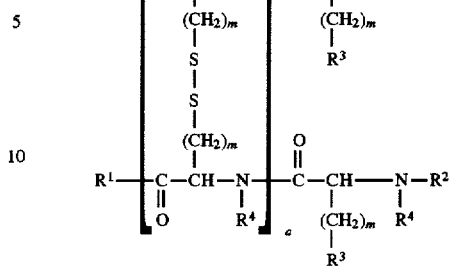

is possible, in which binding units B-1 and B-3 in the peptide can occur singly or repeatedly, identically or differently.

As alkyl groups $R^{20}$, $R^{21}$, $R^{22}$ and $R^{23}$ contained in the $R^{17}$ and $R^{18}$ substituents of the iodized benzene ring, straight-chain or branched-chain or cyclic hydrocarbons with up to 12, preferably up to 10, especially preferably up to 6 C atoms are considered, which are optionally substituted by 1–5, preferably 1–3 hydroxy and/or 1–3 $C_1$–$C_3$ alkoxy and/or 1–3, preferably one, carboxy, sulfo or phosphono group(s).

By name, there can be mentioned, for example, the methyl, hydroxymethyl, ethyl, 2-hydroxyethyl, 2-hydroxy-1-(hydroxymethyl)-ethyl, 1-(hydroxymethyl)-ethyl, propyl, isopropyl, 2-hydroxypropyl, 3-hydroxypropyl, 2,3-dihydroxypropyl, 1,2,3-trihydroxypropyl, butyl, isobutyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl, 1,2,4-trihydroxybutyl, pentyl, cyclopentyl, cyclohexyl, 2,3,4,5,6-pentahydroxyhexyl, 2-methoxyethyl, carboxymethyl, 2-sulfoethyl, phosphonomethyl, 2-carboxyethyl, 10-hydroxydecyl, carboxy, 3-sulfopropyl, 2-phosphonoethyl group.

Suitable alkyl groups for $R^4$, $R^{11}$, $R^{19}$ and $R^{27}$ are, for example, methyl, ethyl, propyl, butyl and isobutyl. Suitable alkyl groups for $R^3$ and $R^8$ include, e.g., those listed above for $R^4$, $R^{11}$, $R^{19}$ and $R^{27}$, as well as pentyl and hexyl.

Suitable alkyl groups for $R^{24}$, $R^{25}$ and $R^{26}$ are, for example, methyl, ethyl, propyl, butyl, isobutyl, pentyl, hexyl, heptyl, octyl, nonyl, decyl, undecyl and dodecyl.

Suitable hydroxyalkyl groups for $R^4$, $R^{11}$ and $R^{19}$ are, for example, hydroxymethyl, 2-hydroxyethyl, 2-hydroxy-1-(hydroxymethyl) -ethyl, 1- (hydroxymethyl) -ethyl, 2-hydroxypropyl, 3-hydroxypropyl, 2,3-dihydroxypropyl, 1,2,3-tri-hydroxypropyl, butyl, isobutyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl and 1,2,4-trihydroxybutyl. Hydroxyl alkyl groups suitable for $R^3$ include, for example, those listed above for $R^4$, $R^{11}$ and $R^{19}$, as well as 2,3,4,5,6-pentahydroxyhexyl.

The subscript n can be 1–100, for example, 1, 2, 3, 4 or 5. The subscript v can also be 1–100, for example, 1, 2, 3, 4, 5, 6, 7, 8, 9, 10, 11, 12, 13, 14, 15, 16, 17, 18, 19 or 20.

The acidic hydrogen atoms of the acid groups contained in the peptide can be replaced completely or partially by cations of inorganic and/or organic bases, amino acids or amino acid amides.

Suitable cations of inorganic bases are, for example, the lithium, the potassium, the calcium, the magnesium and especially the sodium ion. Suitable cations of organic bases are, among others, those of the primary, secondary or tertiary amines, such as, e.g., ethanolamine, diethanolamine, morpholine, glucamine, N,N-dimethylglucamine and especially N-methylglucamine. Suitable cations of amino acids are, for example, those of lysine, of arginine and of ornithine as well as the amides of otherwise acidic or neutral amino acids.

The compounds according to the invention exhibit the above-described desired properties. They contain the number of iodized benzene radicals required for their use as X-ray contrast media. They are distributed only in the vascular space and can therefore mark the latter with the help of X-ray diagnosis.

The iodine content of the compounds according to the invention is on an average 40 wt. %. Thus, in comparison to other macromolecules containing iodoaromatic groups, such as the dextran derivatives described in WO 88/06162 (about 2 to 35%), the iodine content is much higher. The compounds according to the invention can generally be mixed with water in any ratio in contrast to the dextran derivatives described in WO 88/06162, which results in a higher concentration of contrast media in the blood vessels shortly after injection and thus has an advantageous effect on the differentiation of the blood vessels. The value of the osmolality responsible for side effects, such as pain, damage to the blood vessels and cardiovascular disorders, is clearly reduced and is no longer hyperosmolar as otherwise often observed in X-ray contrast media.

With the compounds according to the invention, it is possible to produce macromolecules with defined molecular weight. Such macromolecular contrast media, exactly defined in their molecular size, with iodoaromatic groups were not previously available.

The macromolecules based on dextran, e.g., Dextran 40,000 (Rheomacrodex®), are a mixture of macromolecules of different sizes, whose average molecular weight, e.g., is approximately 40,000 daltons. But, dextran molecules having a molecular weight greater than 50,000 or 60,000 daltons are also present in this mixture. This portion of high-molecular dextran compounds may lie between 5 and 10% of the total amount. As known from the literature (G. Arturson and G. Wallenius, The Renal Clearance of Dextran of Different Molecular Sizes in Normal Humans, Scandinav. J. Clin. & Lab. Investigation 1:81–86, 1964), dextran molecules of this size are no longer glomerularly filtered, and the renal clearance of these molecules is therefore almost zero. Also, the compounds described in patents EP 0206551, EP 0436316 and the compounds described in examples 1, 2 and 3 of WO 93/10824 cannot be completely eliminated because of their high-molecular portions after i.v. administration. But it is expected for diagnostic agents that they be completely eliminated from the body in a short period after intravenous injection. On the other hand, the other compounds described in WO 93/10824 leave the intravascular space too quickly and thus are not suitable as perfusion agents. With the compounds according to the invention, it surprisingly has been possible to make available iodine-containing peptides, which leave the vascular space only slowly, but simultaneously still pass through the capillaries of the kidneys and thus are completely eliminated. Because of the molecular structure, it can be seen that in the first 10 minutes after intravenous administration, the blood concentration of X-ray contrast media (such as, e.g., Ultravist®e) in the extra-cellular space decreases much more quickly than the concentration of the compounds according to the invention (see embodiment 1 and FIG. 1).

The compounds according to the invention are used as contrast media for visualization of the vessels by X-ray diagnostics. It is thus possible to distinguish ischemic tissue from normal tissue. Also, other damages to the blood-tissue barrier can be detected with these compounds. In the case of inflammations and tumors in the brain, the blood-brain barrier is damaged, so that the contrast medium can infiltrate the diseased tissue and thus the diseased tissue can be detected with the X-ray diagnostics. Because of the impermeability of the intact blood-brain barrier, inflammations and tumors could be detected also for small but hydrophilic molecules even with the low-molecular Ultravist®. But if the iodine-containing peptides according to the invention are used in these cases, the dose can be reduced four-fold; since the macromolecules are distributed in a four-fold smaller space, namely only in the vascular space, i.e. to achieve the same concentrations in the blood, a fourth of the dose is sufficient.

At the same time, perfusion measurements, e.g., on the myocardium, can be performed with the compounds according to the invention. This was possible only to a limited extent with the low-molecular compounds such as Ultravist®, since these molecules quickly "run out" into the interstitial space. In the case of the low-molecular compounds, the "running out" into the interstice also often resulted in a poor definition of the image, which can be avoided by the compounds according to the invention. This is of special importance in the visualization of blood vessels in the liver, since here the capillaries are especially permeable. With the compounds according to the invention, it has now been possible also to visualize blood vessels of the liver clearly, with simultaneous use of a small dose of contrast medium. At the same time, the testing time relative to the low-molecular compounds can be greatly prolonged.

The iodine-containing peptides according to the invention can be produced by first preparing peptides with free primary or secondary amino groups first, for example, by the solid phase peptide synthesis (SPPS) method or by the solution method, or by combination of both methods. See, e.g., J. M. Stewart et al., Solid Phase Peptide Synthesis, Pierce Chemical Co. (1984); M. Bodanszky, Peptide Chemisty, Springer Verlag (1993); G. A. Grant, Synthetic Peptides, W. H. Freeman (1992); W. V. Williams et al., Biologically Active Peptides, Technomic Publ. Co. (1993); The Peptides, Analysis, Synthesis, Biology, S. Udenfriend et al., Vol. 7 and earlier volumes, Academic Press (1985); and U.S. Pat. No. 5,229,490.

The product of such synthesis yields a peptide with a desired number of primary or secondary amino groups in the side chains which can then be reacted with compounds of general formula III,

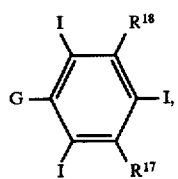 (III)

in which $R^{17}$ and $R^{18}$ have the meanings indicated under general formula I and the carboxy and/or hydroxy groups contained in general formula III are present in protected form and G is a group which contains an activated group capable of reacting with a free amino group(s) of a peptide. Upon reaction with the amino group, G is converted into linker E of the formula

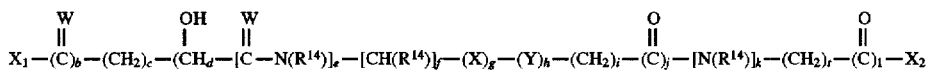

in which W, X, Y, $R^{14}$, b, c, d, e, f, g, h, i, j, k, l and t have the meanings indicated under general formula I, $x_1$ represents the position at which E binds to the peptide, $x_2$ represents the position at which E is bound to the remainder of the compound of formula III, i.e.,

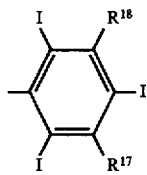

and finally, if in the peptide moiety free amino groups are still present, optionally these groups are reacted with compounds of general formula IV

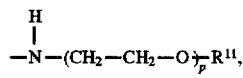 (IV)

in which G has the meaning indicated under general formula III and $R^{28}$ stands for a hydrogen atom, hydroxy or the group

in which $R^{11}$ and p have the meanings indicated under general formula I, and the carboxy and hydroxy groups contained in general formula IV are present in protected form.

As an example for an activated carbonyl group of the feedstocks of general formulas III and IV, there can 15 be mentioned activated carbonyl compounds and α,β-unsaturated compounds such as anhydride, p-nitrophenylester, lactone, N-hydroxysuccinimide ester, acid chloride and acrylic acid derivative. As examples, there can be mentioned the radicals —COCl; —NCO; —NCS;

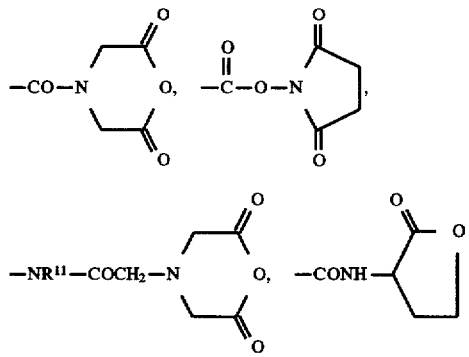

and —NHCO—$CR^{27}$=$CHR^{27}$, in which $R^{11}$ and $R^{27}$ have the meanings indicated under general formula I.

The iodine-containing peptides of general formula I according to the invention, in which substituents $R^2$, $R^3$ and $R^4$ optionally contain protected functional groups, e.g., protected carboxylic acids and/or protected hydroxy groups, and in which $R^1$ stands for a hydroxy group, can be singly or repeatedly reacted with an optionally cyclic oligo- or polyamine after conversion of a compound of general formula I, in which $R^1$ stands for a carboxylic acid, to an activated form, known from peptide chemistry, such as, e.g., to an N-hydroxysuccinimide ester.

The process can be used for oligo- or polymerization of iodine-containing peptides of general formula I, in which $R^1$ stands for a hydroxy group. The "protection" provided by optionally present protective groups, e.g., protected carboxylic acid and/or hydroxy groups, in substituents $R^2$, $R^3$ and $R^4$ of general formula I can then be "removed."

The production of the iodine-containing peptides according to the invention can also occur by preparing an iodine-containing amino acid or a small iodine-containing peptide and using the acid/peptide for synthesis of the desired compounds. Thus, for example, a lysine derivative of general formula V $$R^{12}—E—NH(CH_2)_4—CH(NH—Q)—CO_2H \quad (V),$$

in which $R^{12}$ is an iodized benzene ring as described above, E has the above-indicated meaning and Q represents an amino protective group, is treated so as to activate carboxylic acid groups and is then reacted with amino groups of amino acids bound on resin. The carboxylic acid and hydroxy groups in groups $R^{12}$ and E of the lysine derivative of formula V are in protected form. Q can be one of the amino protective groups typically used in the solid-phase synthesis of peptides, such as, e.g., tertbutyloxycarbonyl, fluorenylmethyloxycarbonyl, carbobenzyloxy, and a variety of others as described in the literature mentioned above.

An example for a suitable lysine derivative which is represented by the general formula V may be the following compound:

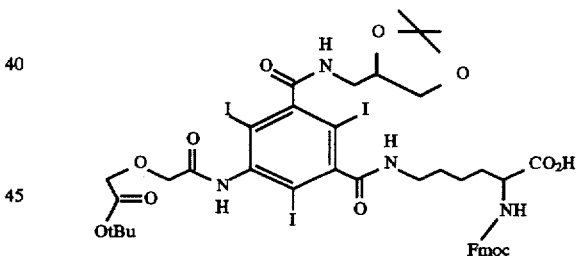

in which the vicinal hydroxy groups are protected as an acetonide, one of the two present carboxy groups is protected as a tert.-butyl ester (OtBu) and the lysine amino group is protected with a fluorenylmethyloxycarbonyl group (Fmoc).

The carboxylic acid can be activated by, e.g., a carbodiimide, 1-benzotriazolyloxy-tri(dimethylamino) phosphoniumhexafluorophosphate or an analog thereof, O-benzo-triazolyl-N,N-N',N'-tetramethyluronium hexafluorophosphate or an analog thereof, acid chloride, a symmetrical acid anhydride, a mixed acid anhydride, an active ester, etc.

After cleavage of protective group Q, this reaction can optionally be repeated or the released amino group(s) can be reacted with the activated form of a carboxylic acid of general formula VI $$R^{12}—E—OH \quad (VI),$$

in which $R^{12}$ and E have the above-indicated meanings.

The release of the iodine-containing peptides according to the invention takes place finally by cleavage from the resin and by cleavage of the protective groups.

As acid protective groups, lower alkyl, aryl and aralkyl groups, for example, the methyl, ethyl, propyl, n-butyl, t-butyl, phenyl, benzyl, diphenylmethyl, triphenylmethyl, bis(p-nitrophenyl)-methyl group as well as trialkylsilyl groups are suitable.

The cleavage of the protective groups takes place according to the processes known to one skilled in the art [see, e.g., E. Wünsch, Methoden der Org. Chemie [Methods of Organic Chemistry] (Houben Weyl), Vol. XV/1, 4th edition 1974, pp. 315 ff], for example, by hydrolysis, hydrogenolysis, alkaline saponification of esters with alkali in aqueous-alcoholic solution at temperatures of 0 to 50° C., acid saponification with mineral acids or in the case of, e.g., tert-butyl esters with the help of trifluoroacetic acid.

As hydroxy protective groups, e.g., the benzyl, 4-methoxybenzyl, 4-nitrobenzyl, trityl, diphenylmethyl, trimethylsilyl, dimethyl-t-butyl-silyl, diphenyl-t-butyl-silyl groups are suitable.

The hydroxy groups can also be present, e.g., as THP-ether, α-alkoxyethylether, MEM-ether or as esters with aromatic or aliphatic carboxylic acids, such as, e.g., acetic acid or benzoic acid. In the case of polyols, the hydroxy groups can also be protected in the form of ketals with, e.g., acetone, acetaldehyde, cyclohexanone or benzaldehyde.

When carboxyl groups are simultaneously present, hydroxy groups can also be present, protected by intramolecular esterification to the corresponding lactones.

The hydroxy protective groups can be released according to the methods in the literature known to one skilled in the art, e.g., by hydrogenolysis, reductive cleavage with lithium/ammonia, acid treatment of the ethers and ketals or alkali treatment of the esters (see, e.g., "Protective Groups in Organic Synthesis," T. W. Greene, John Wiley and Sons 1981).

If one or more thiol groups is or are contained in the peptide, they can be dimerized or oligomerized with the formation of one or more S-S bridges. This reaction can be performed before or after the introduction of the triiodoaromatic compounds to the peptide according to the methods known to one skilled in the art [e.g., J. E. Hesse et al., Chem. Ind. (1965) 680; W. Adam et al., Angew. Chem. Int. Ed. Engl., 27(3), 429 (1988); A. E. Ferentz et al., J. Am. Chem. Soc. 113 (10), 4000 (1991); A. McKillop et al., Tetrahedron Lett. 31 (35), 5007 (1990)].

Thus, the reaction of N,N-bis (carboxymethyl) -amine or -amide-substituted triiodophenyl, present in anhydride form, in liquid reaction media, such as, for example, water, dipolar aprotic solvents, such as diethyl ether, tetrahydrofuran, dioxane, acetonitrile, N-methylpyrrolidone, dimethylformamide, dimethylacetamide and the like or their mixtures takes place by adding amines, such as, e.g., triethylamine, N-ethyldiisopropylamine, N,N-di-methyl-4-aminopyridine. The reaction temperatures are between about −80° C. and 160° C., and temperatures of 20° C. to 80° C. are preferred. The reaction times are between 0.5 hours and 7 days, preferably between 1 hour and 48 hours.

The production of the acid anhydrides can take place according to known processes, e.g., according to the process with acetic anhydride in pyridine described in U.S. Pat. No. 3,660,388 or in DE 16 95 050. But in certain cases, it is advantageous to perform the elimination of water gently with carbodiimides in a suitable solvent, such as, e.g., dimethylformamide or dimethylacetamide.

The reactions of the isocyanate- or isothiocyanate- substituted triiodophenyl take place according to methods known in the literature (DOS 26 10 500, EP 0 431 838), for example, in aprotic solvents, such as, for example, DMSO, DMF, DMA or else in water or hydrous solvent mixtures at temperatures of 0–120°0 C., preferably 20–75°0 C. The reaction times are generally between 1–48 hours, preferably 3–24 hours.

The reaction of triiodophenyl, containing lactone structures, with corresponding polyamines is possible, e.g., analogously to the process for aminolysis of 2-acyl-amino-4-butyrolactones described by T. Sheradsky, Y. Knobler and M. Frankel in J. Org. Chem., 26, 2710 (1961).

Addition reactions of a triiodophenyl exhibiting olefinic substituents CHR=CR—CONH are performed, e.g., according to the instructions indicated in Org. Synth. Coll. Vol. VI, p. 75 (1988), by a triiodized acrylamide being reacted with the desired peptide in polar solvents, such as DMF, DMA, pyridine or ethanol.

The acylations of the terminal amino groups of the polymers of general formula I with triiodophenyl, which contain an acid chloride substituent, are performed according to the processes known to one skilled in the art, e.g., analogously to the instructions in EP 0015867. The reaction is generally performed in polar aprotic solvents, such as, e.g., DMF, DMA, or in mixtures of polar aprotic solvents with water, in the presence of an acid trap, such as, e.g., tertiary amine (e.g., triethylamine, trimethylamine, N,N-dimethylaminopyridine, 1,5-diazabicyclo[4.3.0]-nonene-5 (DBN), 1,5-diazabicyclo[5.4.0]undecene-5 (DBU), alkali-, alkaline-earth carbonate, hydrogen carbonate or -hydroxide (e.g., potassium carbonate, sodium carbonate, lithium hydroxide, potassium hydroxide) at temperatures of about 0–120° C., preferably 20–80° C., and reaction times of about 1–36 hours.

The subsequent acylation or alkylation of the optionally unreacted primary or secondary amino groups takes place analogously to instructions known in the literature, see, e.g., Org. Syn. Coll., Vol. 4, 5 (1963).

The neutralization of the acid groups can be performed with the help of inorganic bases (e.g., hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methyl- and N,N-dimethylglucamine, as well as basic amino acids, such as, for example, lysine, arginine and ornithine or of amides of originally neutral or acidic amino acids.

The iodized aromatic compounds used in the different processes are known or can be easily generated from known compounds.

Thus, e.g., in German laid-open specifications DE 29 28 417 and DE 29 09 439, iodized aromatic compounds are described, which are reacted easily with, e.g., thionyl chloride, to obtain the corresponding acid chloride group-containing aromatic compounds.

Isocyanate- or isothiocyanate-substituted triiodoaromatic compounds can be produced by reaction of the corresponding aniline derivatives with phosgene or thiophosgene to aprotic solvents, such as, e.g., 1,2-dichloroethane, dichloromethane, pyridine, dimethyl sulfoxide, tetrahydrofuran, dioxane, diethyl ether, ethyl acetate (literature: DOS 25 41 491).

Triiodophenyl containing a lactone radical is attained, for example, by reaction of a triiodobenzoyl chloride derivative with 2-amino-4-butyrolactone hydrochloride. A reaction of this type is described, e.g., by J. Brennan and P. J. Murphy in Tetrahedron Lett., 29 (17), 2063 (1988).

Triiodophenyls with an olefinic substituent CHR=CR—CONH can be obtained analogously to the data in Wo 85/01727.

Other aromatic radicals can be produced as described in M. Sovak; Radiocontrast Agents, Handbook of Experimental Pharmacology Vol. 73 (1984), Springer-Verlag, Berlin-Heidelberg-New York-Tokyo or in European Patent EP 0015867.

Pharmaceutical agents that contain at least one of the compounds according to the invention are another object of the invention.

The invention further relates to a process for the production of these agents, which is characterized in that the opacifying substance is brought into a form suitable for the enteral or parenteral administration with the additives and stabilizers usual in galenicals. The pharmaceutical preparation can generally be matched optionally to the specific needs of the user. The concentration of the new X-ray contrast media in the aqueous medium depends completely on the X-ray diagnostic method. The iodine content of the solutions usually lies in the range of about 10–450 mg/ml, preferably 80–200 mg/ml.

The resulting agents are then optionally heat-sterilized. They are administered as a function of the iodine content and of the X-ray diagnostic method or formulation, as discussed above, generally in a dose of about 10 mg of iodine/kg–2000 mg of iodine/kg.

The administration of the aqueous X-ray contrast media solution can take place enterally or parenterally, orally, rectally, intravenously, intraarterially, intravascularly, intracutaneously, subcutaneously (lymphography), subarachnoidally (myelography).

Suitable additives are, for example, physiologically harmless buffers (such as, e.g., tromethamine, bicarbonate, phosphate, citrate), stabilizers (such as, e.g., DTPA, sodium edetate, calcium-disodium edetate), or—if necessary—electrolytes (such as, e.g., sodium chloride) or—if necessary—antioxidants (such as, e.g., ascorbic acid) or else substances for matching the osmolality (such as, e.g., mannitol, glucose).

If suspensions or solutions of the agents according to the invention in water or physiological salt solution are desired for the enteral administration or other purposes, they are mixed with one or more adjuvants (e.g., methyl cellulose, lactose, mannitol) and/or surfactants (e.g., lecithins, Tween®, Myrj®) and/or aromatic substances for taste correction (e.g., ethereal oils), usual in galenicals.

Figure 1:
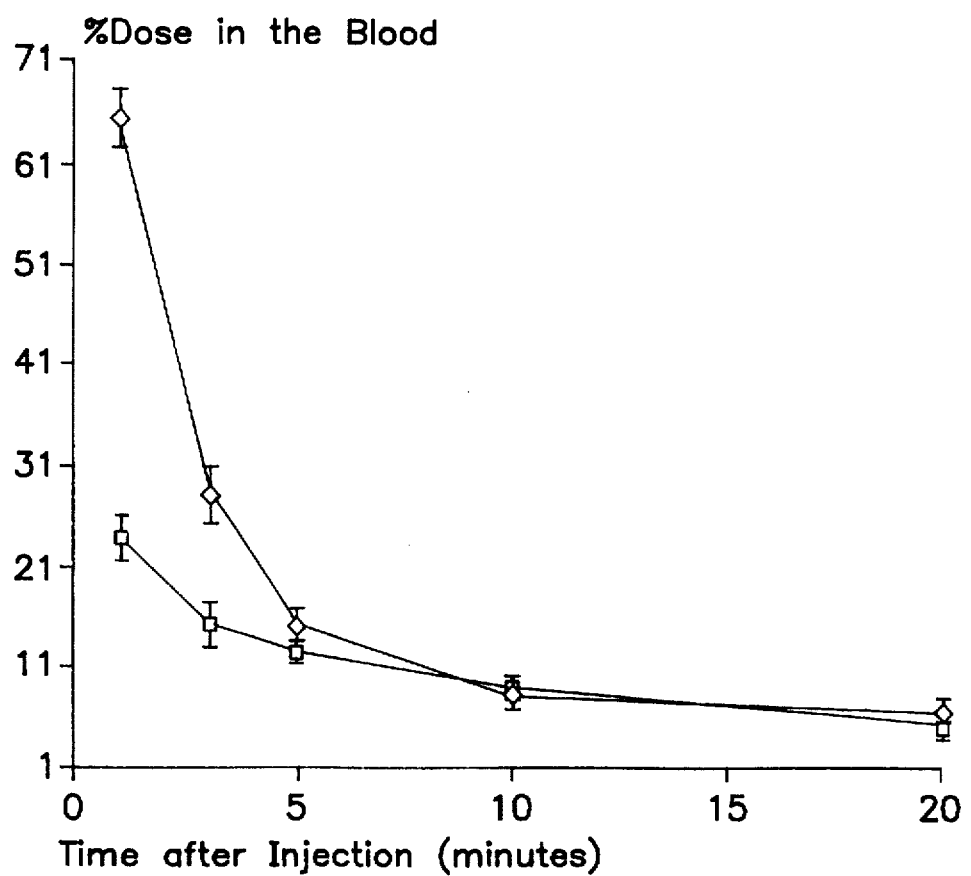
FIG. 1 shows the blood level of the rat as a function of the time after one-time intravenous injection of Ultravist® [□] and 200 mg of I/kg of body weight of the compound of example 4c [◊].

The following production examples are used for a more detailed explanation of the invention without limiting the latter to them.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

Example 1

Dotriacontakis-{3-(3-sodium carboxylatopropionylamino)-5-(2,3-dihydroxypropylcarbamoyl)-2,4,6-triiodobenzoyl} derivative of the lysine-alanine copolymer $(K_3)_8K_4K_2K$-A—OH a) 5-(3-Ethoxycarbonylpropionylamino)-2,4,6-triiodisophthalic acid-N-(2,3-diacetoxy-propyl)-amide-chloride 24.7 g (150 mmol) of succinic acid chloride monoethyl ester is added at room temperature to a suspension of 73.4 g (100 mmol) of 5-amino-2,4,6-triiodisophthalic acid-N-(2,3-diacetoxypropyl)-amide-chloride (EP 0308364) in 500 ml of anhydrous dioxane, stirred with exclusion of moisture. The batch is refluxed for several hours until no more feedstock can be detected according to thin-layer chromatography; then it is concentrated by evaporation, the residue is taken up in dichloromethane and shaken out with saturated aqueous sodium bicarbonate solution. After drying on anhydrous magnesium sulfate, the organic phase is concentrated by evaporation and the residue is recrystallized from ethyl acetate/tert-butyl methyl ether.

Yield: 74.8 g (86.7% of theory) of colorless crystals; Analysis (relative to the solventless substance): Cld: C 29.84 H 2.57 Cl 4.11 I 44.14 N 3.25 O 16.69; Fnd: C 30.19 H 2.63 Cl 4.21 I 44.07 N 3.18 b) Lysine-alanine copolymer $(K_3)_8K_4K_2K$-A—OH 10 g of solid phase peptide synthesis (SPPS) resin substituted with Fmoc-Ala (Fmoc=fluorenylmethyloxycarbonyl) at 0.33 milliequivalents per gram. The Fmoc protecting groups are removed by washing with a mixture of 30% piperidine, 35% toluene and 35% dimethylformamide (DMF) for 12 minutes. Following deprotection, the resin is washed 5 times with DMF, 1 time with methanol and 3 times with dichloromethane (DCM).

The resin is suspended in 70 ml of activator solution (5% N-methyl-morpholine in DMF). Thereafter, added to the suspension are 8.2 g (14 mmoles) of bis-Fmoc-lysine, 7.28 g of coupling agent, benzotriazol-1-yl-oxy-tris-pyrrolidinophosphonium hexafluorophosphate (PyBOP), and 2.14 g of catalyst, 1-hydroxybenzotriazole (HOBT). The reaction medium is mixed for 90 minutes and the resultant product is (Fmoc)$_2$-Lys-Ala-resin, i.e., (Fmoc)$_2$-K-A-resin.

The product of the first coupling reaction is washed 3 times with DCM, 1 time with methanol and 5 times with DMF and then subjected to deprotection using a mixture of 30% piperidine, 35% toluene and 35% DMF. The product obtained from the deprotection is Lys-Ala-resin (K-A-resin). This product is washed 5 times with DMF, 1 time with methanol and 3 times with DCM and then subjected to a second coupling reaction.

The resin is suspended in 140 ml of 5% solution of N-methyl-morpholine in DMF and thereafter 16.54 g (28 mmoles) of bis-Fmoc-lysine, 14.4 g of PyBOP and 4.28 g HOBT. The mixture is reacted and the product obtained is (Fmoc)$_4$-Lys$_2$-Lys-Ala-resin [(Fmoc)$_4$-K$_2$-K-A-resin]. The product is washed 3 times with DCM, 1 time with methanol and 5 times with DMF.

Half of the resultant product containing 1.65 meq of the starting alanine-resin material is subjected to deprotection, a treatment with a mixture of 30% piperidine, 35% toluene, 35% DMF to obtain the deprotected product Lys$_2$-Lys-Ala-resin. The product is then washed 5 times with DMF, 1 time with methanol and 3 times with DCM.

The resin is then suspended in 100 ml of 5% N-methyl-morpholine in DMF to which is added 11.8 g (20 mmoles) bis-Fmoc-Lys, 10.4 g PyBOP and 2.7 g HOBT. The product obtained is (Fmoc)$_8$-Lys$_4$-Lys$_2$-Lys-Ala-resin [(Fmoc)$_8$-K$_4$-K$_2$-K-A-resin].

Following completion of the amplification phase, 8 individual lysine chains containing 3 lysines each are added to the central core. To obtain the individual lysine chains, the cycles of deprotection, washing, coupling and washing are repeated 3 times using, in each case, 14.04 g (30 mmoles) α-Fmoc-ϵ-BOC-lysine (BOC=butoxycarbonyl), 15.6 g PyBOP and 4.6 g HOBT in 100 ml of 10% N-methylmorpholine in DMF. The resultant product, [(α-Fmoc-ϵ-BOC-lysine)-(ϵ-BOC-lysine)$_2$]$_8$-Lys$_4$-Lys$_2$-Lys-Ala-resin, is then subjected to a deprotection procedure to remove the Fmoc groups wherein the product is treated with a mixture of 30% piperidine, 35% toluene and 35% DMF. Thereafter, the product is washed 5 times with DMF, 1 time with methanol and 3 times with DCM.

The resultant resin, [(ϵ-BOC-lysine)-(ϵ-BOC-lysine)$_2$]$_8$-Lys$_4$-Lys$_2$-Lys-Ala-resin, is then subjected to a cleavage reaction during which the BOC protection groups are also removed. The resin is suspended in 100 ml of 5% H$_2$O in trifluoroacetic acid (TFA) for 3–4 hours and then removed by filtration and washed with more of H$_2$O/TFA solution. The washes are combined and the solvents evaporated to obtain a thick oil. Thereafter, about 200 ml of cold ether is added to the thick oil and the peptide TFA salt precipitates. The peptide is collected by filtration, washed with ether, dissolved in water and lyophilized. The product is purified using reverse phase HPLC columns in 0.1% TFA/H$_2$O/acetonitrile solvent.

c) Dotriacontakis-{3-(3-sodium carboxylatopropionylamino)-5-(2,3-dihydroxypropylcarbamoyl)-2,4,6-triiodobenzoyl} derivative of the lysine-alanine copolymer (K$_3$)$_8$K$_4$K$_2$K-A—OH An emulsion, consisting of 7.40 g (0.96 mmol) of the copolymer produced under example 1b), 11.1 mol (80.0 mmol) of triethylamine and 50 ml of water, is slowly instilled in a solution of 39.6 g (45.9 mmol) of the acid chloride, produced under example 1a), in 200 ml of N,N-dimethylformamide, mechanically stirred at room temperature. The batch is stirred for 2 days at room temperature, then mixed with 100 ml of 2n sodium hydroxide solution and stirred for 2 hours at 50° C. After cooling to room temperature, the batch is neutralized with 2n hydrochloric acid, then completely concentrated by evaporation in a vacuum, taken up in water, filtered and then subjected to an ultrafiltration, and low-molecular components are separated by a hollow fiber membrane (H1 P3-20). The aqueous product solution is filtered with a cellulose-membrane filter (pore size 0.45 μm) and freeze-dried.

Yield: 23.3 g (88.1% of theory) of colorless lyophilizate; Analysis (relative to the anhydrous substance): Cld: C 29.10 H 2.79 I 44.12 N 6.44 Na 2.66 O 14.89; Fnd: C 29.22 H 2.83 I 43.96 N 6.61 Na 2.50 O 15.07

Example 2

Dotriacontakis-{3,5-di-(sodium carboxylatomethylcarbamoyl)-2,4,6-triiodophenylcarbamoyl} derivative of the lysine-alanine copolymer (K$_3$)$_8$K$_4$K$_2$K-A—OH a) 5-Amino-2,4,6-triiodisophthalic acid-N,N'-bis-(methoxycarbonylmethyl)-diamide (EP 0129932)

A solution of 59.6 g (100 mmol) of 5-amino-2,4,6-triiodisophthalic acid dichloride in 300 ml of N,N-dimethylformamide is mixed with 27.6 g (220 mmol) of glycine methyl ester hydrochloride and 61.0 ml (440 mmol) of triethylamine. A suspension results, which is stirred overnight at room temperature under argon. After concentration by evaporation of the suspension on a vacuum, the residue is recrystallized from methanol.

Yield: 66.3 g (94.6% of theory); Analysis (relative to the solventless substance): Cld: C 23.99 H 2.01 I 54.31 N 5.99 O 13.69; Fnd: C 23.95 H 2.14 I 54.28 N 6.09 b) 5-Isocyanato-2,4,6-triiodisophthalic acid-N,N'-bis-(methoxycarbonylmethyl)-diamide 147 ml (73.8 mmol) of a 2n toluenic phosgene solution and 2 ml of N,N-dimethylformamide are added to a suspension of 20.7 g (29.5 mmol) of the aniline derivative, produced under example 2a), in 200 ml of 1,2-dichloroethane, stirred at 60° C. oil bath temperature under argon atmosphere. After completion of the reaction of the aniline derivative, the batch is concentrated by evaporation on a vacuum, the residue is absorptively precipitated with anhydrous ethyl acetate, suctioned off under nitrogen atmosphere and dried on an oil pump vacuum.

Yield: 21.5 g (100% of theory) of light beige solid; Analysis (relative to the solventless substance): Cld: C 24.78 H 1.66 I 52.37 N 5.78 O 15.40; Fnd: C 24.82 H 1.73 I 52.35 N 5.70 c) Dotriacontakis-{3,5-di-(sodium carboxylatomethylcarbamoyl)-2,4,6-triiodophenylcarbamoyl} derivative of the lysine-alanine copolymer (K$_3$)$_8$K$_4$K$_2$K-A—OH A solution of 4.47 g (0.58 mmol) of the copolymer, produced under example 1b), and 2.58 ml (18.6 mmol) of triethylamine in 37 ml of anhydrous dimethyl sulfoxide is slowly instilled in a solution of 18.7 g (22.7 mmol) of the isocyanate, produced under example 2b), in 200 ml of anhydrous dimethyl sulfoxide, stirred at room temperature under argon atmosphere. The batch is stirred for 2 days at room temperature, then mixed with 30 ml of 2n sodium hydroxide solution and stirred for 2 hours at 50° C. After cooling to room temperature, the solution is neutralized with 2n hydrochloric acid and largely concentrated by evaporation on a vacuum; the residue is taken up in water, filtered and then subjected to an ultrafiltration, and low-molecular components are separated by a hollow fiber membrane (H1 P3-20). The aqueous product solution is filtered with a cellulose-membrane filter (pore size 0.45 mm) and freeze-dried.

Yield: 13.23 g (81.6% of theory) of yellowish lyophilizate; Analysis (relative to the anhydrous substance): Cld: C 26.11 H 2.07 I 43.77 N 8.00 Na 5.29 O 14.77; Fnd: C 26.28 H 2.18 I 43.58 N 8.11 Na 5.17

Example 3

Dotriacontakis-{3-[(N-carboxymethyl)-sodium carboxylatomethyl-carbamoyl]-5-[N,N-bis-(sodium carboxylatomethyl)]-carbamoyl]-2,4,6-triiodophenylcarbamoyl derivative of the lysine-alanine copolymer (K$_3$)$_8$K$_4$K$_2$K-A—OH a) 5-Amino-2,4,6-triiodisophthalicacid-N,N,N', N'-tetrakis-(methoxycarbonylmethyl)-diamide A solution of 47.2 g (79.2 mmol) of 5-amino-2,4,6-triiodisophthalic acid dichloride in 250 ml of N,N-dimethylformamide is mixed with 34.4 g (174 mmol) of iminodiacetic acid dimethyl-ester-hydrochloride (synthesis according to Dubsky, Graenacher, Chem. Ber. 50, 1693 (1917)) and 48.2 ml (348 mmol) of triethylamine. A suspension results, which is stirred overnight at room temperature under argon. After concentration by evaporation of the suspension on a vacuum, the residue is taken up in dichloromethane and shaken out with aqueous sodium bicarbonate solution. The organic phase is dried with anhydrous magnesium sulfate, filtered and chromatographed after concentration by evaporation on silica gel 60 (mobile solvent: dichloromethane/methanol). The product fractions are evaporated to dryness in a vacuum.

Yield: 57.1 g (85.3% of theory) of colorless solid; Analysis (relative to the solventless substance): Cld: C 28.42 H 2.62 I 45.05 N 4.97 O 18.93; Fnd: C 28.61 H 2.77 I 44.83 N 4.72 b) 5-Isocyanato-2,4,6-triiodisophthalic acid-N,N,N', N'-tetrakis-(methoxycarbonylmethyl)-diamide 45.3 ml (90.5 mmol) of a 2n toluenic phosgene solution and 3 ml of N,N-dimethylformamide are added to a solution of 30.6 g (36.2 mmol) of the aniline derivative, produced under example 3a), in 300 ml of 1,2-dichloroethane at 60° C. oil bath temperature under argon atmosphere. After completion of the reaction of the aniline derivative, the batch is concentrated by evaporation on a vacuum, the residue is absorptively precipitated with tert-butyl methyl ether, suctioned off under nitrogen atmosphere and dried on an oil pump vacuum.

Yield: 30.3 g (96.2% of theory) of reddish solid; Analysis (relative to the solventless substance): Cld: C 28.95 H 2.31 I 43.70 N 4.82 O 20.20; Fnd: C 29.14 H 2.46 I 43.56 N 4.73 c) Dotriacontakis-{3-[(N-carboxymethyl)-sodiumcarboxyl-atomethyl-carbamoyl]-5-[N,N-bis-(sodium carboxylatomethyl)-carbamoyl]-2,4, 6-triiodophenyl-carbamoyl derivative of the lysine-alanine copolymer $(K_3)_8K_4K_2K$-A—OH A solution of 5.32 g (0.69 mmol) of the copolymer, produced under example 1b), and 3.06 ml (22.1 mmol) of triethylamine in 48 ml of anhydrous dimethyl sulfoxide is slowly instilled in a solution of 28.8 g (33.1 mmol) of the isocyanate, produced under example 3b), in 250 ml of anhydrous dimethyl sulfoxide, stirred at room temperature under argon atmosphere. The batch is stirred for 2 days at room temperature, then mixed with 66 ml of 2n sodium hydroxide solution and stirred for 2 hours at 50° C. After cooling to room temperature, the solution is neutralized with 2n hydrochloric acid and then subjected to an ultra-filtration, and low-molecular components are separated by a hollow fiber membrane (H1 P3-20). The aqueous product solution is filtered with a cellulose-membrane filter (pore size 0.45 mm) and freeze-dried.

Yield: 19.2 g (86.4% of theory) of yellowish lyophilizate; Analysis (relative to the anhydrous substance): Cld: C 27.30 H 2.08 I 37.77 N 6.91 Na 6.84 O 19.10; Fnd: C 27.54 H 2.20 I 37.49 N 7.14 Na 6.92

Example 4

Octatetracontakis-{3-sodium carboxylatoformylamino-5-(2, 3-dihydroxypropylcarbamoyl)-2,4,6-triiodobenzoyl} derivative of the lysine-alanine copolymer $(K_5)_8K_4K_2K$-A—OH a) 5-(Ethoxycarbonylformylamino)-2,4, 6-triiodisophthalic acid-N-(2,3-diacetoxypropyl)-amide-chloride 20.5 g (150 mmol) of oxalic acid chloride-monoethyl-ester is added at room temperature to a suspension of 73.4 g (100 mmol) of 5-amino-2,4,6-triiodisophthalic acid-N-(2,3-diacetoxypropyl)-amide-chloride (EP 0308364) in 300 ml of anhydrous dioxane, stirred with exclusion of moisture. The batch is refluxed for several hours, until no more feedstock can be detected according to thin-layer chromatography, then it is concentrated by evaporation, the residue is taken up in dichloromethane and shaken out with saturated aqueous sodium bicarbonate solution. After drying on anhydrous magnesium sulfate, the organic phase is concentrated by evaporation and the residue is recrystallized from ethyl acetate/tert-butyl methyl ether.

Yield: 73.9 g (88.6% of theory) of colorless crystals; Analysis (relative to the solventless substance): Cld: C 27.35 H 2.17 Cl 4.25 I 45.62 N 3.36 O 17.25; Fnd: C 27.33 H 2.28 Cl 4.17 I 45.49 N 3.42 b) Lysine-alanine copolymer $(K_5)_8K_4K_2K$-A—OH 10 g of solid phase synthesis (SPPS) resin substituted with Fmoc-Ala at 0.33 milliequivalents per gram. The Fmoc protecting groups are removed by washing with a mixture of 30% piperidine, 35% toluene and 35% dimethylformamide (DMF) for 12 minutes. Following deprotection, the resin is washed 5 times with DMF, 1 time with methanol and 3 times with dichloromethane (DCM).

The resin is suspended in 70 ml of activator solution (5% N-methyl-morpholine in DMF). Thereafter, added to the suspension are 8.2 g (14 mmoles) of bis-Fmoc-lysine, 7.28 g of coupling agent, benzotriazol-1-yl-oxy-tris-pyr-rolidinophosphonium hexafluorophosphate (PyBOP) and 2.14 g of catalyst, 1-hydroxybenzotriazole (HOBT) . The reaction medium is mixed for 90 minutes and the resultant product is (Fmoc)$_2$-Lys-Ala-resin, i.e., (Fmoc)$_2$-K-A-resin.

The product of the first coupling reaction is washed 3 times with DCM, 1 time with methanol and 5 times with DMF and then subjected to deprotection using a mixture of 30% piperidine, 35% toluene and 35% DMF. The product obtained from the deprotection is Lys-Ala-resin (K-A-resin). This product is washed 5 times with DMF, 1 time with methanol and 3 times with DCM and then subjected to a second coupling reaction.

The resin is suspended in 70 ml of 5% solution of N-methyl-morpholine in DMF and thereafter 16.54 g (25 mmoles) of bis-Fmoc-lysine, 14.4 g of PyBOP and 4.28 g HOBT. The mixture is reacted and the product obtained is (Fmoc)$_4$-Lys$_2$-Lys-Ala-resin [(Fmoc)$_4$-K$_2$-K-A-resin]. The product is washed 3 times with DCM, 1 time with methanol and 5 times with DMF.

Half of the resultant product containing 1.65 meq of the starting alanine-resin material is subjected to deprotection, a treatment with a mixture of 30% piperidine, 35% toluene, 35% DMF to obtain the deprotected product Lys$_2$-Lys-Ala-resin. The product is then washed 5 times with DMF, 1 time with methanol and 3 times with DCM.

The resin is then suspended in 100 ml of 5% N-methyl-morpholine in DMF to which is added 11.8 g (20 mmoles) bis-Fmoc-Lys, 15.6 g PyBOP and 4.6 g HOBT. The product obtained is (Fmoc)$_8$-Lys$_4$-Lys$_2$-Lys-Ala-resin [(Fmoc)$_8$-K$_4$-K$_2$-K-A-resin].

Following completion of the amplification phase, 8 individual lysine chains containing 5 lysines each are added to the central core. To obtain the individual lysine chains, the cycles of deprotection, washing, coupling and washing are repeated 5 times using, in each case, 14.04 g (30 mmoles) α-Fmoc-ε-BOC-lysine, 15.6 g PyBOP and 4.6 g HOBT in 100 ml of 5% N-methyl-morpholine in DMF. The resultant product is [(α-Fmoc-ε-BOC-lysine)-(ε-BOC-lysine)$_4$]$_8$-Lys$_4$-Lys$_2$-Lys-Ala-resin.

The resultant resin is then suspended in 100 ml of 5% H$_2$O and trifluoroacetic acid for 3–4 hours. The resin is removed by filtration and washed. The washes are combined and the solvents evaporated to obtain a thick oil. Thereafter, about 200 ml of cold ether is added to the thick oil and the peptide TFA salt precipitates. The peptide is collected by filtration, washed with ether, dissolved in water and lyophilized. The product is purified using reverse phase HPLC columns and 0.1TFA/H$_2$O/acetonitrile solvent.

c) Octatetracontakis-{3-sodiumcarboxylatoformylamino-5-(2,3-dihydroxypropylcarbamoyl)-2,4,6-triiodobenzoyl} derivative of the lysine-alanine copolymer $(K_5)_8K_4K_2K$-A—OH An emulsion, consisting of 12.05 g (1.04 mmol) of the copolymer produced under example 4b), 10.8 ml (150 mmol) of triethylamine and 80 ml of water, is slowly instilled in a solution of 62.6 g (75.0 mmol) of the acid chloride, produced under example 4a), in 350 ml of N,N-dimethyl-formamide, mechanically stirred at room temperature. The batch is stirred for 2 days at room temperature, then mixed with 150 ml of 2n sodium hydroxide solution and stirred for 2 hours at 50° C. After cooling to room temperature, the solution is neutralized with 2n hydrochloric acid and concentrated by evaporation in a vacuum; the residue is taken up in water, filtered and subjected to an ultrafiltration, and low-molecular components are separated by a hollow fiber membrane (H1 P3-20). The aqueous product solution is filtered on a cellulose-membrane filter (pore size 0.45 mm) and freeze-dried.

Yield: 38.2 g (91.4% of theory) of colorless lyophilizate; Analysis (relative to the anhydrous substance): Cld: C 27.23 H 2.40 I 45.58 N 6.67 Na 2.75 O 15.36; Fnd: C 27.41 H 2.53 I 45.29 N 6.78 Na 2.63

Example 5

Octatetracontakis-{3-(4-sodium carboxylato-3-oxabutyrylamino)-5-(2,3-dihydroxy-propylcarbamoyl)-2,4,6-triiodobenzoyl} derivative of the lysine-alanine copolymer $(K_5)_8K_4K_2K$-A—OH a) Diglycolic acid chloride-monoisopropyl ester 46.4 g (400 mmol) of diglycolic acid anhydride is added to 24.0 g (400 mmol) of anhydrous isopropanol with exclusion of moisture. The temperature of the exothermal reaction is moderated with a water bath to 90°–100° C. After 1 hour, the reaction mixture is allowed to cool and mixed with 32.0 ml (440 mmol) of thionyl chloride and 0.1 ml of N,N-dimethylformamide and allowed to stir for 15 hours at room temperature and for 1 hour at 50° C. The title compound is obtained by distillation at 0.01 torr and a boiling temperature of 100°–101° C.

Yield: 67.6 g (86.8% of theory) of colorless liquid Gas chromatography (100% method): content 96.4%; Analysis (relative to the solventless substance): Cld: C 43.20 H 5.70 Cl 18.22 O 32.88; Fnd: C 43.34 H 5.83 Cl 18.01 b) 5-[4-(2-Methylethyloxycarbonyl)-3-oxabutyrylamino]-2,4,6-triiodisophthalic acid-N-(2,3-diacetoxypropyl)-amide-chloride 29.2 g (150 mmol) of the acid chloride, produced according to example 5a), is added at room temperature to a suspension of 73.4 g (100 mmol) of 5-amino-2,4,6-triiodisophthalic acid-N-(2,3-diacetoxypropyl)-amide-chloride (EP 0308364) in 500 ml of anhydrous dioxane, stirred with exclusion of moisture. The batch is refluxed for several hours until no more feedstock can be detected according to thin-layer chromatography, then it is concentrated by evaporation, the residue is taken up in dichloromethane and shaken out with saturated, aqueous sodium bicarbonate solution. After drying on anhydrous magnesium sulfate, the organic phase is concentrated by evaporation and the residue is recrystallized from ethyl acetate/tert-butyl methyl ether.

Yield: 68.2 g (76.4% of theory) of colorless crystals; Analysis (relative to the solventless substance): Cld: C 29.60 H 2.71 Cl 3.97 I 42.65 N 3.14 O 32.88; Fnd: C 29.77 H 2.83 Cl 3.92 I 42.41 N 3.38 c) Octatetracontakis-{3-(4-sodiumcarboxylato-3-oxabuty-rylamino)-5-(2,3-dihydroxy-propylcarbamoyl)-2,4,6-triiodo-benzoyl} derivative of the lysine-alanine copolymer $(K_5)_8K_4K_2K$-A—OH An emulsion, consisting of 7.99 g (0.69 mmol) of the copolymer produced under example 4b), 13.9 ml (100 mmol) of triethylamine and 50 ml of water, is slowly instilled in a solution of 44.6 g (50.0 mmol) of the acid chloride, produced under example 5b), in 200 ml of N,N-dimethylformamide, mechanically stirred at room temperature. The batch is stirred for 2 days at room temperature, then mixed with 100 ml of 2n sodium hydroxide solution and stirred for 2 hours at 50° C. After cooling to room temperature, the solution is neutralized with 2n hydrochloric acid and concentrated by evaporation on a vacuum. The residue is taken up in water, filtered and subjected to an ultrafiltration, and low-molecular components are separated by a hollow fiber membrane (H1 P3-20). The aqueous product solution is filtered with a cellulose-membrane filter (pore size 0.45 mm) and freeze-dried.

Yield: 24.02 g (82.6% of theory) of colorless lyophilizate; Analysis (relative to the anhydrous substance): Cld: C 28.64 H 2.74 I 43.35 N 6.21 Na 2.62 O 16.43; Fnd: C 28.75 H 2.85 I 43.12 N 6.33 Na 2.50

Example 6

Octatetracontakis-{3-[N,N-bis-(sodium carboxylatomethyl)-carbamoyl)]-5-methoxyacetylamino-2,4,6-triiodobenzoyl} derivative of the lysine-alanine copolymer $(K_5)_8K_4K_2K$-A—OH a) 5-Methoxyacetylamino-2,4,6-triiodisophthalic acid-N,N-bis-(methoxycarbonylmethyl)-amide-chloride A solution of 66.8 g (100 mmol) of 5-methoxyacetylamino-2,4,6-triiodisophthalic acid dichloride (EP 0015867) in 300 ml of anhydrous N,N-dimethylformamide is mixed with 21.75 g (110 mmol) of iminodiacetic acid dimethyl ester-hydrochloride (synthesis according to Dubsky, Graenacher, Chem. Ber. 50, 1693 (1917)) and 30.5 ml (220 mmol) of triethylamine. A suspension results, which is stirred for 14 hours at room temperature under argon. The batch is taken up in dichloromethane, shaken out once with water, twice with 2n aqueous citric acid and once with aqueous sodium bicarbonate solution. The organic phase is dried on anhydrous magnesium sulfate and concentrated by evaporation in a vacuum. By instillation of tert-butyl ether in the concentrated solution, the title compound can be precipitated as crystalline solid, which is suctioned off and dried in a vacuum.

Yield: 57.4 g (72.4% of theory); Analysis (relative to the solventless substance): Cld: C 25.76 H 2.04 Cl 4.47 I 48.04 N 3.54 O 16.15; Fnd: C 25.82 H 2.11 Cl 4.48 I 48.01 N 3.38 b) Octatetracontakis-{3-[N,N-bis-(sodium carboxylatomethyl)-carbamoyl)]-5-methoxy-acetylamino-2,4,6-triiodobenzoyl} derivative of the lysine-alanine copolymer $(K_5)_8K_4K_2K$-A—OH An emulsion, consisting of 7.42 g (0.64 mmol) of the copolymer produced under example 4b), 13.9 ml (100 mmol) of triethylamine and 50 ml of water, is slowly instilled in a solution of 36.3 g (45.8 mmol) of the acid chloride, produced under example 6a), in 200 ml of N,N-dimethylformamide, mechanically stirred at room temperature. The batch is stirred for 2 days at room temperature, then mixed with 100 ml of 2n sodium hydroxide solution and stirred for 2 hours at 50° C. After cooling to room temperature, the solution is neutralized with 2n hydrochloric acid and concentrated by evaporation on a vacuum. The residue is taken up in water and subjected to an ultrafiltration, and low-molecular components are separated by a hollow fiber membrane (H1 P3-20).

The aqueous product solution is filtered with a cellulose-membrane filter (pore size 0.45 mm) and freeze-dried.

Yield: 25.0 g (91.0% of theory) of colorless lyophilizate; Analysis (relative to the anhydrous substance): Cld: C 27.96 H 2.34 I 42.33 N 6.20 Na 5.11 O 16.05; Fnd: C 28.22 H 2.48 I 42.08 N 6.31 Na 4.98

Example 7

Octatetracontakis-{N-[3,5-di-(acetylamino)-2,4,6-triiodobenzoyl] -N-(sodium carboxylatomethyl)-glycyl derivative of the lysine-alanine copolymer $(K_5)_8K_4K_2K$-A—OH a) 3,5-Dinitrobenzoyl-N,N-bis-(carboxymethyl)-amide 133.1 g (1.00 mol) of iminodiacetic acid is dissolved in 1.50 1 of 2n sodium hydroxide solution and mixed with 230.6 g (1.00 mol) of 3,5-dinitrobenzoyl chloride with mechanical stirring. A dark red solution results, from which the title compound is precipitated by acidification with semiconcentrated hydrochloric acid. The precipitate is suctioned off, washed with water and dried in a vacuum.

Yield: 260.5 g (79.6% of theory) of colorless crystals; Analysis (relative to the anhydrous substance): Cld: C 40.38 H 2.77 N 12.84 O 44.01; Fnd: C 40.42 H 2.85 N 12.63 b) 3,5-Diaminobenzoyl-N,N-bis-(carboxymethyl)-amide 32.7 g (100 mmol) of the dinitro compound described under example 7a) is introduced in 500 ml of methanol, mixed with 1.6 g of palladium catalyst (10% palladium on activated carbon) and hydrogenated with hydrogen with shaking. After taking up the theoretical amount of hydrogen, it is filtered off from the catalyst and evaporated to dryness. The residue is further reacted without purification.

Yield: 26.7 g (100% of theory) of colorless solid; Analysis (relative to the solventless substance): Cld: C 49.44 H 4.90 N 15.72 O 29.93; Fnd: C 49.40 H 4.98 N 15.68 c) 3,5-Diamino-2,4,6-triiodobenzoyl-N,N-bis-(carboxymethyl)-amide 24.7 g (92.4 mmol) of the compound produced under example 7b) is mixed in 200 ml of water and with 150 ml of a 2n iodomonochloride solution within 30 minutes. The mixture is stirred for 12 hours at room temperature and the precipitate formed is suctioned off. The solid is suspended in water, treated with 10 g of sodium hydrogen sulfite and again isolated. The material is dissolved in 300 ml of water by adding 30% sodium hydroxide solution at pH 8, mixed with 2 g of activated carbon, stirred for 5 hours and filtered. By acidification of the filtrate with concentrated hydrochloric acid, a precipitate is formed, which is suctioned off and dried in a vacuum.

Yield: 40.1 g (67.3% of theory) of colorless solid; Analysis (relative to the anhydrous substance): Cld: C 20.49 H 1.59 I 59.03 N 6.52 O 12.40; Fnd: C 20.61 H 1.63 I 58.86 N 6.68 d) 3,5-Bis-(acetylamino)-2,4,6-triiodobenzoyl-N,N-bis-(carboxymethyl)-amide 38.6 g (59.9 mmol) of the compound produced under example 7c) is introduced in a mixture of 180 ml of acetic anhydride and 0.5 ml of concentrated sulfuric acid. After stirring overnight at room temperature, diethyl ether is added and the solid formed is filtered off. The solid is dissolved in 300 ml of water by adding 30% sodium hydroxide solution at pH 9 and then again precipitated by acidification with concentrated hydrochloric acid at pH 1. The precipitate is suctioned off and dried in a vacuum.

Yield: 29.9 g (68.6% of theory) of colorless solid; Analysis (relative to the anhydrous substance): Cld: C 24.71 H 1.94 I 52.22 N 5.76 O 15.36; Fnd: C 24.65 H 2.03 I 52.31 N 5.65 e) N-[3,5-Bis-(acetylamino)-2,4,6-triiodobenzoyl]-2,6-dioxomorpholine 28.1 g (38.5 mmol) of the compound produced under example 7d) is dissolved in 56 ml of anhydrous pyridine, mixed with 7.3 ml (77 mmol) of acetic anhydride and stirred with exclusion of moisture for 10 hours at room temperature. By instillation of anhydrous diethyl ether, the anhydride formed is precipitated, filtered off and dried in a vacuum.

Yield: 27.4 g (100% of theory) of light beige solid; Analysis (relative to the solventless substance): Cld: C 25.34 H 1.70 I 53.55 N 5.91 O 13.50; Fnd: C 25.21 H 1.83 I 53.58 N 5.86 0 13.73 f) Octatetracontakis-{N-[3,5-di-(acetylamino)-2,4,6-triiodobenzoyl] -N- (sodium carboxylatomethyl)-glycyl derivative of the lysine-alanine copolymer $(K_5)_8K_4K_2K$-A—OH An emulsion, consisting of 5.8 g (0.50 mmol) of the copolymer produced under example 4b), 11.1 ml (80.0 mmol) of triethylamine and 30 ml of water, is slowly instilled in a solution of 25.6 g (36.0 mmol) of the anhydride, produced under example 7e), in 200 ml of N,N-dimethylformamide, mechanically stirred at room temperature. The batch is stirred for 2 days at room temperature, then neutralized with 2n hydrochloric acid and concentrated by evaporation on a vacuum. The residue is filtered and subjected to an ultrafiltration, and low-molecular components are separated by a hollow fiber membrane (H1 P3-20). The aqueous product solution is filtered with a cellulosemembrane filter (pore size 0.45 mm) and freeze-dried.

Yield: 18.7 g (90.4% of theory); Analysis (relative to the anhydrous substance): Cld: C 29.23 H 2.68 I 44.25 N 8.11 Na 2.67 O 13.06; Fnd: C 29.45 H 2.74 I 44.07 N 8.24 Na 2.49

Example 8

Octaoctakis-{3-[(N-sodium carboxylatomethyl)-methoxyacetylamino-5-(2,3-dihydroxy-propylcarbamoyl)-2,4,6-triiodobenzoyl} derivative of the lysine-alanine copolymer $(K_{10})_8K_4K_2K$-A—OH a) 5-Methoxyacetylamino-2,4,6-triiodisophthalic acid-N-(2,3-diacetoxypropyl)-amide-chloride 24.7 g (150 mmol) of methoxyacetyl chloride is added at room temperature to a suspension of 73.4 g (100 mmol) of 5-amino-2,4,6-triiodisophthalic acid-N-(2,3-diacetoxypropyl)-amide-chloride (EP 0308364) in 500 ml of anhydrous dioxane, stirred with exclusion of moisture. The batch is refluxed for several hours, until no more feedstock can be detected according to thin-layer chromatography, then it is concentrated by evaporation, the residue is taken up in dichloromethane and shaken out with saturated aqueous sodium bicarbonate solution. After drying on anhydrous magnesium sulfate, the organic phase is concentrated by evaporation and the residue is recrystallized from ethyl acetate/tert-butyl methyl ether.

Yield: 73.2 g (90.7% of theory) of colorless crystals; Analysis (relative to the solventless substance): Cld: C 26.81 H 2.25 Cl 4.40 I 47.21 N 3.47 O 15.87; Fnd: C 26.79 H 2.32 Cl 4.48 I 47.13 N 3.44 b) 5-Methoxyacetylamino-2,4,6-triiodisophthalic acid-N-(2,3-dihydroxypropyl)-monoamide 60.6 g (75.1 mmol) of the acid chloride produced under example 8a) is introduced in 376 ml of a in sodium hydroxide solution and stirred vigorously for about 45 minutes under nitrogen atmosphere. The completeness of the conversion is checked by thin-layer chromatography and the product solution is used for the next stage without working-up.

c) N-Carboxymethyl-5-methoxyacetylamino-2,4,6-triiodiso-phthalic acid-N'-(2,3-dihydroxypropyl)-monoamide The solution of the feedstock (75.1 mmol) produced according to example 8b) is mixed under nitrogen atmosphere with 17.5 g (150.2 mmol) of the sodium salt of chloroacetic acid and stirred for about 18 hours at 90° C. The solution is adjusted to pH 1.with 2n hydrochloric acid and completely concentrated by evaporation. The residue is chromatographed on silica gel 60 [mobile solvent: dichloromethane/methanol/acetic acid (2:2:1)]. The product fractions are evaporated to dryness in a vacuum and the residue is recrystallized from' methanol/isopropanol.

Yield: 47.7 g (83.3% of theory) of colorless crystals; Analysis (relative to the solventless substance): Cld: C 25.22 H 2.25 I 49.96 N 3.68 O 18.90; Fnd: C 25.31 H 2.51 I 49.82 N 3.72 d) N-Methoxycarbonylmethyl-5-methoxyacetylamino-2, 4,6-triiodisophthalic acid-N'-(2,3-dihydroxypropyl)-monoamide 45.8 g (60.1 mmol) of the compound produced under example 8c) is introduced in 150 ml of anhydrous methanol and stirred under nitrogen atmosphere. 5.6 ml (6.6 mmol) of dimethyl sulfite is instilled with stirring. The batch is stirred for 4 hours at room temperature and refluxed for 1 hour. Then, it is concentrated by evaporation, the residue is absorptively precipitated with isopropanol, filtered off and dried in a vacuum.

Yield: 41.2 g (88.4% of theory) of colorless crystals; Analysis (relative to the solventless substance): Cld: C 26.31 H 2.47 I 49.06 N 3.61 O 18.55; Fnd: C 26.21 H 2.35 I 49.13 N 3.53 e) N-Methoxycarbonylmethyl-5-methoxyacetylamino-2, 4,6-triiodisophthalic acid-N'-(2,3-diacetoxypropyl)-monoamide 38.2 g (49.2 mmol) of the compound produced under example 8d) is stirred in a mixture of 16.3 ml (172 mmol) of acetic anhydride and 150 ml of dioxane with exclusion of moisture. 0.60 g (4.9 mmol) of 4-N,N-dimethylaminopyridine is added and stirred for 2 hours at 50° C. Then, the batch is concentrated by evaporation, the residue is absorptively precipitated with ethyl acetate/tert-butyl methyl ether, filtered off and dried in a vacuum.

Yield: 37.0 g (87.4% of theory) of colorless solid; Analysis (relative to the solventless substance): Cld: C 29.32 H 2.70 I 44.26 N 3.26 O 20.46; Fnd: C 29.38 H 2.77 I 44.17 N 3.30 f) N-Methoxycarbonylmethyl-5-methoxyacetylamino-2, 4,6-triiodisophthalic acid-N'-(2,3-diacetoxypropyl)-amide-chloride 35.6 g (41.4 mmol) of the compound described under example 8e) is introduced in 150 ml of 1,2-dichloroethane. 0.1 ml of N,N-dimethylformamide and 4.50 ml (62.1 mmol) of thionyl chloride are added to the suspension stirred with exclusion of moisture at room temperature. The batch is refluxed until no more gas generation can be observed. The now present solution is concentrated by evaporation on a vacuum, the residue is taken up in dichloromethane and shaken out with saturated, aqueous sodium bicarbonate solution. The organic phase is dried on anhydrous magnesium sulfate and filtered. By instillation of tert-butyl methyl ether in the filtrate that is concentrated by evaporation, a colorless precipitate is obtained, which is suctioned off and dried in a vacuum.

Yield: 30.6 g (84.1% of theory) of colorless solid; Analysis (relative to the solventless substance): Cld: C 28.71 H 2.52 Cl 4.04 I 43.33 N 3.19 O 18.21; Fnd: C 28.81 H 2.80 Cl 4.28 I 43.17 N 3.21 g) Lysine-alanine copolymer $(K_{10})_8K_4K_2K$-A—OH 10 g of SPPS resin substituted with Fmoc-Ala at 0.33 milliequivalents per gram. The Fmoc protecting groups are removed by washing with a mixture of 30% piperidine, 35% toluene and 35% dimethylformamide (DMF) for 12 minutes. Following deprotection, the resin is washed 5 times with DMF, 1 time with methanol and 3 times with dichloromethane (DCM).

The resin is suspended in 70 ml of activator solution (5% N-methyl-morpholine in DMF). Thereafter, added to the suspension are 8.2 g (14 mmoles) of bis-Fmoc-lysine, 7.28 g of coupling agent, benzotriazol-1-yl-oxy-tris-pyrrolidinophosphonium hexafluorophosphate (PyBOP), and 2.14 g of catalyst, 1-hydroxybenzotriazole (HOBT). The reaction medium is mixed for 90 minutes and the resultant product is $(Fmoc)_2$-Lys-Ala-resin, i.e., $(Fmoc)_2$-K-A-resin.

The product of the first coupling reaction is washed 3 times with DCM, 1 time with methanol and 5 times with DMF and then subjected to deprotection using a mixture of 30% piperidine, 35% toluene and 35% DMF. The product obtained from the deprotection is Lys-Ala-resin (K-A-resin). This product is washed 5 times with DMF, 1 time with methanol and 3 times with DCM and then subjected to a second coupling reaction.

The resin is suspended in 70 ml of 5% solution of N-methyl-morpholine in DMF and thereafter 16.54 g (25 mmoles) of bis-Fmoc-lysine, 14.4 g of PyBOP and 4.28 g HOBT. The mixture is reacted and the product obtained is $(Fmoc)_4$-Lys$_2$-Lys-Ala-resin [$(Fmoc)_4$-K$_2$-K-A-resin]. The product is washed 3 times with DCM, 1 time with methanol and 5 times with DMF.

Half of the resultant product containing 1.65 meq of the starting alanine-resin material is subjected to deprotection, a treatment with a mixture of 30% piperidine, 35% toluene, 35% DMF to obtain the deprotected product Lys$_2$-Lys-Ala-resin. The product is then washed 5 times with DMF, 1 time with methanol and 3 times with DCM.

The resin is then suspended in 100 ml of 5% N-methylmorpholine in DMF to which is added 11.8 g (20 mmoles) bis-Fmoc-Lys, 15.6 g PyBOP and 4.6 g HOBT. The product obtained is $(Fmoc)_8$-Lys$_4$-Lys$_2$-Lys-Ala-resin [$(Fmoc)_8$-K$_4$-K$_2$-K-A-resin].

Following completion of the amplification phase, 8 individual lysine chains containing 10 lysines each are added to the central core. To obtain the individual lysine chains, the cycles of deprotection, washing, coupling and washing are repeated 10 times using, in each case, 14.04 g (30 mmoles) α-Fmoc-ε-BOC-lysine, 15.6 g PyBOP and 4.6 g HOBT in 100 ml of 5% N-methyl-morpholine in DMF. The resultant product is [(α-Fmoc-ε-BOC-lysine)-(ε-BOC-lysine)$_9$]$_8$-Lys$_4$-Lys$_2$-Lys-Ala-resin.

The resultant resin is then suspended in 100 ml of 5% H$_2$O and trifluoroacetic acid for 3–4 hours. The resin is removed by filtration and washed. The washes are combined and the solvents evaporated to obtain a thick oil. Thereafter, about 200 ml of cold ether is added to the thick oil and the peptide TFA salt precipitates. The peptide is collected by filtration, washed with ether, dissolved in water and lyophilized. The product is purified using reverse phase HPLC columns and 0.1% TFA/H$_2$O acetonitrile solvent.

h) Octaoctakis-{3-[(N-sodiumcarboxylatomethyl)-methoxyacetylamino-5-(2,3-dihydroxypropylcarbamoyl)-2, 4,6-triiodobenzoyl} derivative of the lysine-alanine copolymer $(K_{10})_8K_4K_2K$-A—OH An emulsion, consisting of 3.83 g (0.18 mmol) of the copolymer produced under example 8g), 5.5 ml (40 mmol) of triethylamine and 30 ml of water, is slowly instilled in a solution of 21.2 g (24.1 mmol) of the acid chloride, produced under example 8f), in 100 ml of N,N-dimethylformamide, mechanically stirred at room temperature. The batch is stirred for 2 days at room temperature, then mixed with 60 ml of 2n sodium hydroxide solution and stirred for 2 hours at 50° C. After cooling to room temperature, the solution is neutralized with 2n hydrochloric acid and concentrated by evaporation on a vacuum. The residue is taken up in water and subjected to an ultrafiltration, and low-molecular components are separated by a hollow fiber membrane (H1 P3-20). The aqueous product solution is filtered with a cellulose-membrane filter (pore size 0.45 mm) and freeze-dried.

Yield: 11.8 g (84.3% of theory) of colorless lyophilizate; Analysis (relative to the anhydrous substance): Cld: C 30.40 H 3.01 I 40.88 N 6.44 Na 2.65 O 16.61; Fnd: C 30.52 H 3.11 I 40.72 N 6.51 Na 2.58

Example 9
Dotetracontakis-{3,5-[N,N-bis-(sodium carboxylatomethyl)-carbamoyl)]-2,4,6-triiodophenylthiocarbamoyl} derivative of the lysine-alanine copolymer $(K_{20})_2$K-A—OH a) 5-Isothiocyanato-2,4,6-triiodisophthalic acid-N,N'-bis-(methoxycarbonylmethyl)-diamide 20 ml of polyvinylpyridine (Reillex), 50 ml of water and 3.66 ml (49.4 mmol) of thiophosgene in 30 ml of 1,2-dichloroethane are added to a suspension of 17.3 g (24.7 mmol) of the aniline derivative, described under example 2a), in 170 ml of 1,2-dichloroethane, stirred at room temperature. After three hours of stirring at 50° C., the batch is taken up in dichloromethane, the organic phase is separated, dried on anhydrous magnesium sulfate and filtered. The filtrate is concentrated by evaporation on a vacuum, the residue is absorptively precipitated with ethyl acetate, suctioned off and dried on a vacuum.

Yield: 16.6 g (90.7% of theory) of light beige solid; Analysis (relative to the solventless substance): Cld: C 24.25 H 1.63 I 51.24 N 5.66 O 12.92 S 4.32 ; Fnd: C 24.33 H 1.74 I 51.12 N 5.65 S 4.53 b) Lysine-alanine copolymer $(K_{20})_2$K-A—OH 10 g of SPPS resin substituted with Fmoc-Ala at 0.33 milliequivalents per gram. The Fmoc protecting groups are removed by washing with a mixture of 30% piperidine, 35% toluene and 35% dimethylformamide (DMF) for 12 minutes. Following deprotection, the resin is washed 5 times with DMF, 1 time with methanol and 3 times with dichloromethane (DCM).

The resin is suspended in 70 ml of activator solution (5% N-methyl-morpholine in DMF). Thereafter, added to the suspension are 8.2 g (14 mmoles) of bis-Fmoc-lysine, 7.28 g of coupling agent, benzotriazol-1-yl-oxy-tris-pyrrolidinophosphonium hexafluorophosphate (PyBOP), and 2.14 g of catalyst, 1-hydroxybenzotriazole (HOBT). The reaction medium is mixed for 90 minutes and the resultant product is (Fmoc)$_2$-Lys-Ala-resin, i.e., (Fmoc)$_2$-K-A-resin. The product of the coupling reaction is washed 3 times with DCM, 1 time with methanol and 5 times with DMF and then subjected to deprotection using a mixture of 30% piperidine, 35% toluene and 35% DMF. The product obtained from the deprotection is Lys-Ala-resin (K-A-resin). This product is washed 5 times with DMF, 1 time with methanol and 3 times with DCM.

Following completion of this amplification phase, 8 individual lysine chains containing 20 lysines each are added to the central core. To obtain the individual lysine chains, the cycles of deprotection, washing, coupling and washing are repeated 20 times using, in each case, 14.04 g (30 mmoles) α-Fmoc-ε-BOC-lysine, 15.6 g PyBOP and 4.6 g HOBT in 100 ml of 5% N-methyl-morpholine in DMF. The resultant product is [(α-Fmoc-ε-BOC-lysine)-(ε-BOC-lysine)$_{19}$]$_8$-Lys$_4$-Lys$_2$-Lys-Ala-resin.

The resultant resin is then suspended in 100 ml of 5% H$_2$O and trifluoroacetic acid for 3–4 hours. The resin is removed by filtration and washed. The washes are combined and the solvents evaporated to obtain a thick oil. Thereafter, about 200 ml of cold ether is added to the thick oil and the peptide TFA salt precipitates. The peptide is collected by filtration, washed with ether, dissolved in water and lyophilized. The product is purified using reverse phase HPLC columns and 0.1% TFA/H$_2$O acetonitrile solvent.

c) Dotetracontakis-{3,5-[N,N-bis-(sodium carboxylatometh-yl)-carbamoyl)]-2,4,6-triiodophenylthiocarbamoyl} derivative of the lysine-alanine copolymer $(K_{20})_2$K-A—OH A solution of 3.45 g (0.34 mmol) of the cascade amine, produced under example 9b), and 2.0 ml (14 mmol) of triethylamine in 30 ml of dimethyl sulfoxide is instilled in a solution of 15.8 g (21.3 mmol) of the isothiocyanate, produced under example 9a), in 80 ml of dimethyl sulfoxide, mechanically stirred at room temperature. The batch is stirred for 2 days at room temperature, then mixed with 30 ml of 2n sodium hydroxide solution and stirred for 2 hours at 50° C. After cooling to room temperature, the solution is neutralized with 2n hydrochloric acid and concentrated by evaporation in a vacuum. The residue is taken up in water and subjected to an ultrafiltration, and low-molecular components are separated by a hollow fiber membrane (H1 P3-20). The aqueous product solution is filtered with a cellulose-membrane filter (pore size 0.45 mm) and freeze-dried.

Yield: 11.3 g (89.4% of theory) of colorless lyophilizate; Analysis (relative to the anhydrous substance): Cld: C 25.65 H 2.03 I 42.96 N 7.87 Na 5.19 O 12.68 S 3.62; Fnd: C 25.79 H 2.09 I 42.86 N 7.93 Na 5.24 S 3.50

Example 10
Dotetracontakis-{3-sodium carboxylatomethylcarbamoyl-5-[(N-methoxyacetyl)-methylamino]-2,4,6-triiodobenzoyl derivative of the lysine-alanine copolymer $(K_{20})_2$K-A—OH a) N-Methoxyacetyl-5-methylamino-2,4,6-triiodisophthalic acid-N'-ethoxycarbonylmethyl-amide-chloride A solution of 68.2 g (100 mmol) of N-methoxyacetyl-5-methylamino-2,4,6-triiodisophthalic acid dichloride (EP 0015867) in 500 ml of N,N-dimethylformamide is mixed with 14.0 g (100 mmol) of glycine ethyl ester hydrochloride (production according to D. A. Hoogwater, M. Peereboom, Tetrahedron, 46, 5325–5332 (1990)) and 10.1 g (100 mmol) of triethylamine. A suspension results, which is stirred overnight under argon at room temperature. Then, it is concentrated by evaporation and the residue is chromatographed on silica gel 60 with dichloromethane/ethyl acetate. After concentration by evaporation of the product fractions, a colorless solid is obtained, which is dried in a vacuum.

Yield: 53.4 g (71.49% of theory); Analysis (relative to the solventless substance): Cld: C 25.68 H 2.15 Cl 4.74 I 50.87 N 3.74 O 12.83; Fnd: C 25.84 H 2.31 Cl 4.62 I 50.59 N 3.69 b) Dotetracontakis-{3-sodiumcarboxylatomethylcarbamoyl-5-[(N-methoxyacetyl)-methylamino]-2,4,6-triiodobenzoyl derivative of the lysine-alanine copolymer $(K_{20})_2$K-A—OH A solution of 3.58 g (0.69 mmol) of the copolymer, described in example 9b), in 30 ml of water and 6.41 g (63.3 mmol) of triethylamine are instilled simultaneously in a solution of 31.6 g (42.2 mmol) of the acid chloride, produced under example 10a), in 200 ml of N,N-dimethylformamide, mechanically stirred at room temperature under argon atmosphere. The batch is stirred for 2 days at room temperature, then mixed with 50 ml of 2N sodium hydroxide solution and stirred for 1.5 hours at 50° C. After the cooling to room temperature, the solution is neutralized with 2N hydrochloric acid and concentrated by evaporation in a vacuum. The residue is taken up in water and subjected to an ultrafiltration, and low-molecular components are separated by a hollow fiber membrane (H1 P3-20). The aqueous product solution is filtered with a cellulose-membrane filter (pore size 0.45 µm) and freeze-dried.

Yield: 20.8 g (85.8% of theory) of colorless lyophilizate; Analysis (relative to the anhydrous substance): Cld: C 28.73 H 2.65 I 45.69 N 6.68 Na 2.76 O 13.49; Fnd: C 28.88 H 2.72 I 45.45 N 6.74 Na 2.69

Example 11

Octatetracontakis-{N-methoxyacetyl-3-methylamino-5-(2-sodium sulfonatoethylcarbamoyl)-2,4,6-triiodobenzoyl} derivative of the lysine-alanine copolymer $(K_5)_8K_4K_2K$-A—OH a) N-Methoxyacetyl-5-methylamino-2,4,6-triiodisophthalic acid-N'-(2-bromethyl)-amide-chloride A solution of 68.2 g (100 mmol) of N-methoxyacetyl-5-methylamino-2,4,6-triiodisophthalic acid dichloride (EP 0015867) in 500 ml of N,N-dimethylformamide is mixed with 20.5 g (100 mmol) of 2-bromethylamine-hydrobromide and 20.2 g (200 mmol) of triethylamine. A suspension results, which is stirred overnight under argon at room temperature. Then, it is concentrated by evaporation and the residue is chromatographed on silica gel 60 with dichloromethane/ethyl acetate. After concentration by evaporation of the product fractions, a colorless solid is obtained, which is dried in a vacuum.

Yield: 55.3 g (71.88% of theory); Analysis (relative to the solventless substance): Cld: C 21.86 H 1.70 Br 10.39 Cl 4.61 I 49.49 N 3.64 O 8.32; Fnd: C 21.84 H 1.81 Br 10.48 Cl 4.62 I 49.59 N 3.69 b) Octatetracontakis-{N-methoxyacetyl-3-methylamino-5-(2-sodium sulfonatomethylcarbamoyl)-2,4,6-triiodobenzoyl} derivative of the lysine-alanine copolymer $(K_5)_8K_4K_2K$-A—OH A solution of 5.93 g (0.97 mmol) of the copolymer, described in example 4b), in 50 ml of water and 12.6 ml (90.9 mmol) of triethylamine are simultaneously instilled in a solution of 53.8 g (69.9 mmol) of the acid chloride, produced under example 11a), in 200 ml of N,N-dimethylformamide, mechanically stirred at room temperature. Thereafter, a solution of 47.7 g (378 mmol) of sodium sulfite in 200 ml of water is instilled into the batch. The batch is stirred for 3 days at room temperature. Then, it is filtered and the filtrate is subjected to an ultrafiltration, and low-molecular components are separated by a hollow fiber membrane (H1 P3-20). The aqueous product solution is filtered with a cellulose-membrane filter (pore size 0.45 μm) and freeze-dried.

Yield: 24.6 g (59.8% of theory) of colorless lyophilizate; Analysis (relative to the anhydrous substance): Cld: C 27.11 H 2.73 I 43.10 N 6.31 Na 2.60 O 14.53 S 3.63; Fnd: C 27.34 H 3.80 I 43.01 N 6.47 Na 2.49 S 3.44

Example 12

Dotriacontakis-{3,5-bis-(disodium phosphonatomethylcarba-moyl)-2,4,6-triiodaryl-carbamoyl} derivative of the lysine-alanine copolymer $(K_3)_8K_4K_2K$-A—OH a) 5-Amino-2,4,6-triiodisophthalicacid-N,N'-bis-(diethylphosphonomethyl)-diamide A solution of 59.6 g (100 mmol) of 5-amino-2,4,6-triiodisophthalic acid dichloride (DOS 2926428) in 300 ml of N,N-dimethylformamide is mixed with 36.8 g (220 mmol) of aminomethanephosphonic acid diethyl ester and 61.0 ml (440 mmol) of triethylamine. A suspension results, which is stirred overnight at room temperature under argon. After the concentration by evaporation of the suspension in a vacuum, the residue is recrystallized from methanol.

Yield: 59.8 g (69.8% of theory); Analysis (relative to the solventless substance): Cld: C 25.22 H 3.29 I 44.42 N 4.90 P 7.23 O 14.93; Fnd: C 25.16 H 3.41 I 44.26 N 4.78 P 7.17 b) 5-Isocyanato-2,4,6-triiodisophthalic acid-N,N'-bis-(diethylphosphonomethyl)-diamide 147 ml (73.8 mmol) of a 2n toluenic phosgene solution and 2 ml of N,N-dimethylformamide are added to a suspension of 25.7 g (30 mmol) of the aniline derivative, produced under example 12a), in 200 ml of 1,2-dichloroethane, stirred at 65° C. oil bath temperature under argon atmosphere. After completion of the reaction of the aniline derivative, the batch is concentrated by evaporation in a vacuum, the residue is absorptively precipitated with anhydrous ethyl acetate, suctioned off under nitrogen atmosphere and dried in an oil pump vacuum.

Yield: 25.6 g (96.7% of theory) of light beige solid; Analysis (relative to the solventless substance): Cld: C 25.84 H 2.97 I 43.11 N 4.76 P 7.02 O 16.31; Fnd: C 25.72 H 3.08 I 42.98 N 4.59 P 6.91 c) Dotriacontakis-{3,5-bis-(disodium phosphonatomethyl-carbamoyl)-2,4,6-triiodaryl carbamoyl} derivative of the lysine-alanine copolymer $(K_3)_8K_4K_2K$-A—OH A solution of 4.08 g (0.53 mmol) of the copolymer, produced under example 1b), and 2.35 ml (17.0 mmol) of triethylamine in 47 ml of anhydrous dimethyl sulfoxide is slowly instilled in a solution of 22.5 g (25.5 mmol) of the isocyanate, produced under example 12b), in 220 ml of anhydrous dimethyl sulfoxide, stirred at room temperature under argon atmosphere. The batch is stirred for 3 days at room temperature, then concentrated by evaporation in a high vacuum, mixed with 14.11 ml (110.5 mmol) of bromotrimethylsilane and stirred for 26 hours at 45° C. The crude product is mixed drop by drop with 150 ml of water and stirred for 4 hours at room temperature. After neutralization with sodium hydroxide solution, it is filtered and the filtrate is subjected to an ultrafiltration, and low-molecular components are separated by a hollow fiber membrane (H1 P3-20). The aqueous product solution is filtered with a cellulose-membrane filter (pore size 0.45 mm) and freeze-dried.

Yield: 12.7 g (75.9% of theory) of yellowish lyophilizate; Analysis (relative to the anhydrous substance): Cld: C 20.60 H 1.83 I 38.62 N 7.06 Na 9.33 O 16.28 P 6.28; Fnd: C 20.73 H 2.09 I 38.30 N 7.23 Na 8.98 P 6.21

Example 13

Production and dimerization (with a disulfide bridge) of dotriacontakis-{3-(3-sodium carboxylatopropionylamino)-5-(2,3-dihydroxypropylcarbamoyl)-2,4,6-triiodobenzoyl} derivative of the lysine-proline-cysteine-alanine copolymer $(K_3)_8K_4K_2K$-$P_{10}$-C-A a) Production of the lysine-proline-cysteine-alanine co-polymer This peptide is synthesized using the same chemistry and principles as described in Example 1(b).

Beginning with 10 g of solid phase peptide synthesis resin substituted with Fmoc-Ala at 0.43 meq of alanine per gram, the resin is subjected to synthesis cycles using in each cycle a 3-fold excess of appropriately protected amino acids. In each cycle, the resin is washed with a mixture of 30% piperidine, 35% toluene, and 35% DMF to remove Fmoc protecting groups. Thereafter, the product is washed (5 times with DMF, 1 time with methanol and 3 times with DCM). The resin is suspended in activator solution to which is added the appropriate protected amino acid for coupling (3-fold excess) along with coupling agent PyBOP (3-fold excess) and catalyst HOBT (3-fold excess). The product is then washed (3 times with DCM, 1 time with methanol, 5 times with DMF) and then the cycle begins again.

In the first cycle, the protected amino acid is Fmoc-Cys-Trt—OH (13 mmol) wherein Trt is trityl (i.e., triphenylmethyl). In the next 10 cycles, the protected amino acid is Fmoc-Pro—OH and in the 12th cycle, the protected amino acid is bis-α,ε-Fmoc-Lys—OH. After completion of these 12 cycles, the resultant product is $(Fmoc)_2$-K-$(P)_{10}$-C(Trt)-A-resin.

The synthesis is continued with two more amplification cycles using, respectively, 26 and 40 mmoles bis-Fmoc-Lys—OH as the protected amino acid. The resultant product is $(Fmoc)_8K_4K_2K-(P)_{10}$-C(Trt)-A-resin.

Following the amplification phase, 8 individual lysine chains containing 3 lysines each are constructed onto the central core in 3 cycles using in each cycle 80 mmoles of α-Fmoc-∈-BOC-Lys—OH as the protected amino acid. The resultant product is [α-Fmoc-∈-BOC-K-(∈-BOC-K)$_2$]$_8$-K$_4$-K$_2$-K-(P)$_{10}$-C(Trt)-A-resin.

After deprotection of Fmoc groups (using mixture of 30% piperidine, 35% toluene, 35% DMF) and appropriate washes (5 times with DMF, 1 time with methanol, 3 times with DCM), the peptide is cleaved (with the concomitant removal of BOC and Trt groups) by suspending the resin in a solution of 82.5% TFA, 5% H$_2$O, 5% ethylene dithiol, 5% thioanisole and 2.5% phenol (v/v). The free peptide is isolated in a manner similar to that described in Example 1(b).

b) Production and dimerization (with a disulfide bridge) of dotriacontakis-{3-(3-sodiumcarboxylatopropionylamino)-5-(2,3-dihydroxypropylcarbamoyl)-2,4,6-triiodobenzoyl} derivative of the lysine-proline-cysteine-alanine copolymer $(K_3)_8K_4K_2K-P_{10}$-C-A An emulsion, consisting of 8.43 g (0.96 mmol) of the copolymer produced under example 13a), 13.9 ml (100 mmol) of triethylamine and 50 ml of water, is slowly instilled in a solution of 39.6 g (45.9 mmol) of the acid chloride, produced under example 1a), in 200 ml of N,N-dimethylformamide, mechanically stirred at room temperature. The batch is stirred for 2 days at room temperature, then mixed with 100 ml of 2n sodium hydroxide solution and stirred for 2 hours at 50° C. After cooling to room temperature, the batch is neutralized with 2n hydrochloric acid, then completely concentrated by evaporation on a vacuum, taken up in water, filtered and then subjected to an aerobic dialysis, and low-molecular components are separated by a hollow fiber membrane (H1 P3-20). The completion of the dimerization is checked by gel permeation chromatography (GPC). The aqueous product solution is filtered with a cellulose-membrane filter (pore size 0.45 μm) and freeze-dried.

Yield: 22.9 g (83.6% of theory) of colorless lyophilizate; Analysis (relative to the anhydrous substance): Cld: C 30.23 H 2.94 I 42.47 N 6.74 Na 2.56 O 14.95; Fnd: C 30.38 H 3.02 I 42.19 N 6.83 Na 2.46 O 15.11

Example 14

Octatriacontakis-{3-(4-sodium carboxylato-3-oxabutyryl-amino)-5-(2,3-dihydroxy-propylcarbamoyl)-2,4,6-triiodobenzoyl}-tetrakis-(4-sodium carboxylato-3-oxabutyryl) derivative of the lysine-alanine copolymer $(K_{20})_2$K-A—OH A solution of 12.1 g (1.19 mmol) of the copolymer, produced according to example 9b), in 40 ml of water and 16.6 ml (120 mmol) of triethylamine are simultaneously instilled in a solution of 44.6 g (50.0 mmol) of the acid chloride, produced under example 5b), in 250 ml of N,N-dimethylformamide, mechanically stirred at room temperature under argon atmosphere. The batch is stirred for 2 days at room temperature, then mixed with 1.16 g (10.0 mmol) of diglycolic acid anhydride and stirred for another 24 hours. Then, 50 ml of 2N sodium hydroxide solution is added and stirred for 1.5 hours at 50° C. After the cooling to room temperature, the solution is neutralized with 2N hydrochloric acid and filtered. The residue is taken up in water and subjected to an ultrafiltration, and low-molecular components are separated by a hollow fiber membrane (H1 P3-20). The aqueous product solution is filtered with a cellulose-membrane filter (pore size 0.45 μm) and freeze-dried.

Yield: 41.1 g (89.1% of theory) of colorless lyophilizate; Analysis (relative to the anhydrous substance): Cld: C 26.38 H 2.56 I 47.17 N 5.75 Na 2.49 O 15.65; Fnd: C 26.44 H 2.60 I 47.05 N 5.88 Na 2.37

Example 15

Octatetracontakis-{3-(4-sodium carboxylato-3-oxabutyryl-amino)-5-(2,3-dihydroxy-propylcarbamoyl)-2,4,6-triiodobenzoyl} derivative of the lysine-alanine copolymer [(∈-K)$_5$]$_8$K$_4$K$_2$K-A—OH a) Lysine-alanine copolymer |(∈-K)$_5$]$_8$K$_4$K$_2$K-A—OH 10 g of solid phase synthesis (SPPS) resin substituted with Fmoc-Ala at 0.33 milliequivalents per gram. The Fmoc protecting groups are removed by washing with a mixture of 30% piperidine, 35% toluene and 35% dimethylformamide (DMF) for 12 minutes. Following deprotection, the resin is washed 5 times with DMF, 1 time with methanol and 3 times with dichloromethane (DCM).

The resin is suspended in 70 ml of activator solution (5% N-methyl-morpholine in DMF). Thereafter, added to the suspension are 8.2 g (14 mmoles) of bis-Fmoc-lysine, 7.28 g of coupling agent, benzotriazol-1-yl-oxy-tris-pyrrolidinophosphonium hexafluorophosphate (PyBOP) and 2.14 g of catalyst, 1-hydroxybenzotriazole (HOBT). The reaction medium is mixed for 90 minutes and the resultant product is (Fmoc)$_2$-Lys-Ala-resin, i.e., (Fmoc)$_2$-K-A-resin.

The product of the first coupling reaction is washed 3 times with DCM, 1 time with methanol and 5 times with DMF and then subjected to deprotection using a mixture of 30% piperidine, 35% toluene and 35% DMF. The product obtained from the deprotection is Lys-Ala-resin (K-A-resin). This product is washed 5 times with DMF, 1 time with methanol and 3 times with DCM and then subjected to a second coupling reaction.

The resin is suspended in 70 ml of 5% solution of N-methyl-morpholine in DMF and thereafter 16.54 g (25 mmoles) of bis-Fmoc-lysine, 14.4 g of PYBOP and 4.28 g HOBT. The mixture is reacted and the product obtained is (Fmoc)$_4$-Lys$_2$-Lys-Ala-resin [(Fmoc)$_4$-K$_2$-K-A-resin]. The product is washed 3 times with DCM, 1 time with methanol and 5 times with DMF.

Half of the resultant product containing 1.65 meq of the starting alanine-resin material is subjected to deprotection, a treatment with a mixture of 30% piperidine, 35% toluene, 35% DMF to obtain the deprotected product Lys$_2$-Lys-Ala-resin. The product is then washed 5 times with DMF, 1 time with methanol and 3 times with DCM.

The resin is then suspended in 100 ml of 5% N-methyl-morpholine in DMF to which is added 11.8 g (20 mmoles) bis-Fmoc-Lys, 15.6 g PyBOP and 4.6 g HOBT. The product obtained is (Fmoc)$_8$-Lys$_4$-Lys$_2$-Lys-Ala-resin [(Fmoc)$_8$-K$_4$-K$_2$-K-A-resin].

Following completion of the amplification phase, 8 individual lysine chains containing 5 lysines each are added to the central core. To obtain the individual lysine chains, the cycles of deprotection, washing, coupling and washing are repeated 5 times using, in each case, 14.04 g (30 mmoles) α-BOC-∈-Fmoc-lysine, 15.6 g PyBOP and 4.6 g HOBT in 100 ml of 5% N-methyl-morpholine in DMF. The resultant product is [(α-BOC-∈-Fmoc-lysine)-(∈-Fmoc-lysine)$_4$]$_8$-Lys$_4$-Lys$_2$-Lys-Ala-resin.

The resultant resin is then suspended in 100 ml of 5% H$_2$O and trifluoroacetic acid for 3–4 hours. The resin is removed by filtration and washed. The washes are combined and the solvents evaporated to obtain a thick oil. Thereafter, about 200 ml of cold ether is added to the thick oil and the peptide TFA salt precipitates. The peptide is collected by filtration, washed with ether, dissolved in water and lyophilized. The product is purified using reverse phase HPLC columns and 0.1% TFA/H$_2$O acetonitrile solvent.

b) Octatetracontakis-{3-(4-sodiumcarboxylato-3-oxabutyrylamino)-5-(2, 3-dihydroxy-propylcarbamoyl)-2,4, 6-triiodo-benzoyl} derivative of the lysine-alanine copolymer [($\epsilon$-K)$_5$]$_8$K$_4$K$_2$—A—OH An emulsion, consisting of 8.11 g (0.70 mmol) of the copolymer produced under example 15a), 13.9 ml (100 mmol) of triethylamine and 50 ml of water, is slowly instilled in a solution of 44.6 g (50.0 mmol) of the acid chloride, produced under example 5b), in 200 ml of N,N-dimethylfor-mamide, mechanically stirred at room temperature. The batch is stirred for 2 days at room temperature, then mixed with 100 ml of 2n sodium hydroxide solution and stirred for 2 hours at 50° C. After cooling to room temperature, the solution is neutralized with 2n hydrochloric acid and concentrated by evaporation on a vacuum. The residue is taken up in water, filtered and subjected to an ultrafiltration, and low-molecular components are separated by a hollow fiber membrane (H1 P3-20). The aqueous product solution is filtered with a cellulose-membrane filter (pore size 0.45 mm) and freeze-dried.

Yield: 25.4 g (88.1% of theory) of colorless lyophilizate

Analysis (relative to the anhydrous substance): Cld: C 28.64 H 2.74 I 43.35 N 6.21 Na 2.62 O 16.43 Fnd: C 28.83 H 2.77 I 43.06 N 6.38 Na 2.45

Embodiment 1

The blood level in the rat was determined after one-time intravenous injection of 300 mg of I/kg of body weight of Ultravist®[■], and 200 mg of I/kg of body weight of the compound of example 4c [◇]. The data represent the average value from three animals each.

Standardized to the administered dose, the blood concentration of Ultravist® decreases—especially in the first 10 minutes after administration—very much more quickly than the concentration of the polymer of example 4. This can be attributed to the quick spreading of the small molecule Ultravist® from the blood space to the interstitial space, while the compound of example 4 remains very much longer in the blood space.

Despite the high molecular weight, the compound of example 4 shows a complete elimination from the body of the rat (dose 100 mg of I/kg); for 14 days after administration, only a retention of altogether 0.36% of the dose was measured in the organs liver, kidney and spleen as well as in the remainder of the body. The elimination of the compound of example 4 took place mainly through the kidney. In this case, the absence of higher-molecular contaminants in the compound is demonstrated by the complete elimination and the small retention in the body (see FIG. 1).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make variious changes and modifications of the invention to adapt it to various usages and conditions.

What is claimed is:

1. An iodine-containing peptide of general formula I $$R^1 \left[ \begin{array}{c} O \\ \| \\ C-CH-(CH_2)_q-N \\ | \qquad\qquad\qquad | \\ (CH_2)_m \qquad\quad R^4 \\ | \\ R^3 \end{array} \right]_a R^2 \qquad (I)$$

in which

R$^1$ stands for the group —OR$^5$ or $$-N\begin{array}{c}R^{25}\\ \\R^{26}\end{array};$$

R$^2$ stands for a dendrimere having $$\sum_{k=0}^{n-1} 2^k$$

reproduction units R, n represents the number of generations and is 1–100, q is 0–6, R is a radical of formula II $$\left[ \begin{array}{c} O \qquad\quad (CH_2)_w-N-\alpha \\ \| \qquad\qquad\qquad\quad | \\ -C-CH \qquad\qquad\quad H \\ \qquad\quad \backslash \\ \qquad\qquad (CH_2)_m-N-\alpha \\ \qquad\qquad\qquad\qquad\quad | \\ \qquad\qquad\qquad\qquad\quad H \end{array} \right] \qquad (II)$$

wherein

α for each generation up to n–1 is, in each case, a reproduction unit R, and for the nth generation is, in each case, the group $$-\left[ \begin{array}{c} O \\ \| \\ C-CH-(CH_2)_w-N \\ | \qquad\qquad\qquad | \\ (CH_2)_m \qquad\quad R^4 \\ | \\ R^3 \end{array} \right]_v R^6;$$

wherein v is 1–100;

R$^3$ stands for a hydrogen atom, hydroxy, phenyl, straight-chain or branched C$_1$–C$_6$ alkyl optionally substituted by hydroxy, or a group $$-N-R^7, -N-C\begin{array}{c}NH\\ \|\\ \\NH-R^7\end{array}, \begin{array}{c}\text{benzimidazolyl group}\end{array}$$
$$\quad\ \ \backslash\ \ \ |\\ \quad R^{11}\ H$$

$$\begin{array}{c}C=CH\\ | \qquad\backslash\\ N\qquad\ N-R^7, -S-R^8, -S-S-R^9, -C-R^{10},\\ \ \ \backslash\ \ /\\ \ \ \ CH\end{array} \qquad \begin{array}{c}O\\ \|\end{array}$$

or

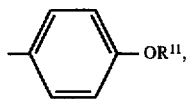

and

R$^4$ stands for a hydrogen atom, C$_1$–C$_4$ alkyl or C$_1$–C$_8$ acyl optionally monosubstituted or polysubstituted by hydroxy, or the group —(CH$_2$)$_n$—COOH or

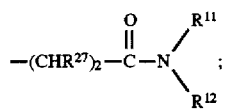

R$^3$ and R$^4$ can alternatively together with the nitrogen atom form a 5- or 6-membered ring, wherein each R$^3$ group can be the same or different and each R$^4$ group can be the same or different;

R$^5$ stands for a hydrogen atom, a saccharide, an oligosaccharide, or a polysaccharide; or if q in each case is 0, R$^3$ in each case can also be either —NR$^{11}$—CO— or —S—S— connected to a further backbone of the formula

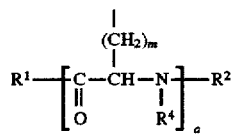

to yield a dimer structure of the formula

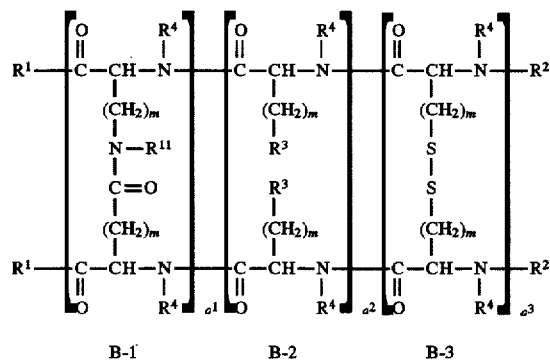

wherein a$^1$, a$^2$ and a$^3$, in each case, is 0–200, a$^1$+a$^2$+a$^3$=a, the individual B-1, B-2 and B-3 units can be in any order, and each of the B-1, B-2 and B-3 units can be the same or different;

R$^6$ and R$^7$, independently in each case, stand for the group

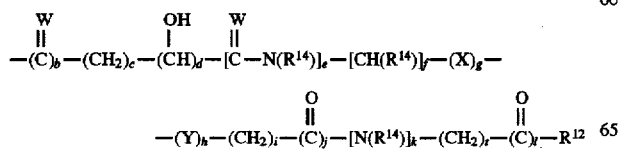

or the group

or the group

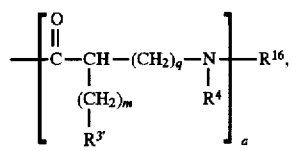

X stands for an oxygen or sulfur atom or the group

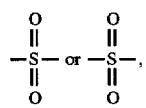

Y stands for the group

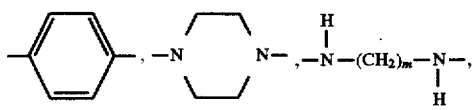

or

W stands for an oxygen or sulfur atom,

R$^8$ stands for a hydrogen atom, C$_1$–C$_6$ alkyl or C$_1$–C$_{10}$ acyl,

R$^9$ means the group

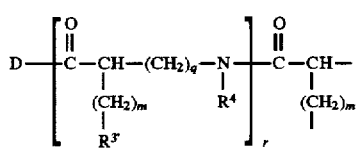

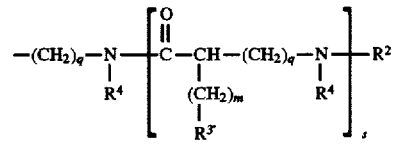

R$^{10}$ means hydroxy or the group

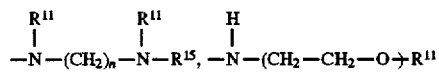

or

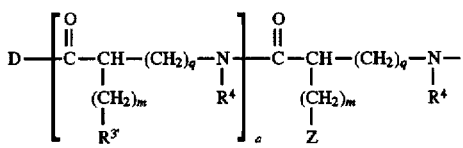

D means hydroxy or the group

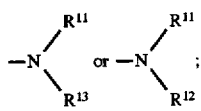

Z means the group

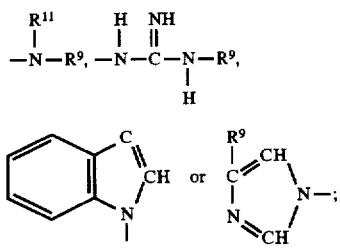

$R^{11}$ stands for a hydrogen atom, $C_1$–$C_4$ alkyl optionally mono- or polysubstituted by hydroxy, or the group —$(CH_2)_n$—COOH.

$R^{12}$ stands for a hydrogen atom or hydroxy or the group

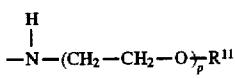

or an iodized benzene ring of the formula

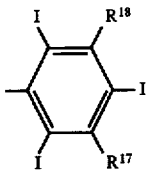

$R^{13}$ stands for the group

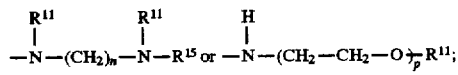

$R^{14}$ stands for a hydrogen atom, a carboxy group or a $C_1$–$C_{20}$ alkyl optionally interrupted one or more times by an oxygen atom and/or mono- or polysubstituted by a hydroxy, carboxy, sulfono, phosphono and/or $C_1$–$C_3$ alkoxy group, or the group

$R^{15}$ has the meaning mentioned under $R^6$ and $R^7$.
$R^{16}$ stands for the group

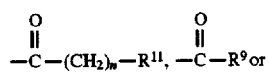

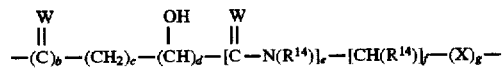

—continued

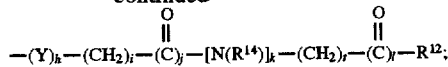

$R^{17}$ and $R^{18}$, respectively independently of one another, stand for a hydrogen atom or a group —$CONR^{20}R^{21}$ or —$NR^{22}COR^{23}$ $R^{19}$ means a $C_1$–$C_4$ alkyl optionally interrupted one or more times by an oxygen atom and/or optionally mono- or polysubstituted by a hydroxy, carboxy, sulfono, phosphono and/or $C_1$–$C_3$ alkoxy group, $R^{20}$ and $R^{21}$, independently of one another, stand for a hydrogen atom, a $C_1$–$C_{12}$ alkyl, $C_3$–$C_{12}$ cycloalkyl, $C_3$–$C_{12}$ cycloalkyl-$C_{1-12}$ alkyl, or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a hydroxy, $C_1$–$C_3$ alkoxy, carboxy, sulfo and/or phosphono group, or $R^{20}$ and $R^{21}$ alternatively can together with the nitrogen atom form a 5- or 6-membered ring, which optionally can contain an oxygen atom or the group

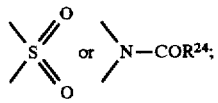

$R^{22}$ stands for a hydrogen atom or a $C_1$–$C_{12}$ alkyl, $C_3$–$C_{12}$ cycloalkyl, $C_3$–$C_{12}$ cycloalkyl-$C_{1-12}$ alkyl, or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a carboxy, sulfono, phosphono group and/or hydroxy group, $R^{23}$ stands for a carboxy group or a straight chain or branched chain $C_1$–$C_{12}$ alkyl, which is optionally interrupted one or more times by an oxygen atom, a carbonyl group and/or an imino group wherein the latter is optionally substituted by a carboxymethyl group, and/or the $C_{1-12}$-alkyl is optionally mono- or polysubstituted by a hydroxy, carboxy, sulfono, phosphono and/or $C_1$–$C_3$ alkoxy group, and $R^{24}$ stands for a carboxy group or a $C_1$–$C_{12}$ alkyl optionally interrupted one or more times by a carbonyl group and/or optionally mono- or polysubstituted by a hydroxy, $C_1$–$C_3$ alkoxy, carboxy, sulfono or phosphono group, $R^{25}$ and $R^{26}$ are the same or different and stand for $C_1$–$C_{20}$ alkyl optionally interrupted by one or more nitrogen or oxygen atoms, and the nitrogen atoms can be substituted by a hydrogen atom or by the group

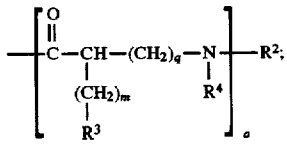

$R^{27}$ stands for a hydrogen atom or $C_1$–$C_4$ alkyl,
$R_{3'}$ stands for a hydrogen atom, hydroxy, phenyl, $NR_2^{11}$, straight-chain or branched alkyl optionally substituted by hydroxy, or $R^3$ and $R^4$ can together with the nitrogen atom form a 5-or 6-membered ring, a in each case stands for 0–200, b, e, g, h, j, k and l are, in each case, the same or different and stand for 0 or 1, c and i are, in each case, the same or different and stand for 0 to 10, d, f, m, p, t and w are, in each case, the same or different and stand for 0 to 6, n stands for 0 to 20, and r and s are, in each case, the same or different and stand for 0 to 100, wherein the total sum of all subscripts a, r, s and v is 10–200, and wherein at least 10 iodized benzene radicals are contained in the peptide;

or a salt thereof with physiologically acceptable organic bases, inorganic bases, amino acids and amino acid amides.

2. An iodine-containing peptide according to claim 1, wherein $R^1$ stands for hydroxy, $R^2$ stands for a dendrimere having $$\sum_{k=0}^{n-1} 2^k$$

reproduction units R, n represents the number of generations and is 1–100, q is 0–6, R is a radical of formula II

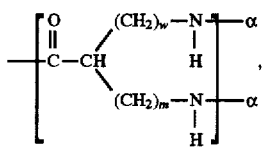

(II)

wherein

α for each generation up to n−1 is, in each case, a reproduction unit R, and for the nth generation is, in each case, the group

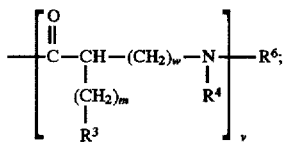

wherein v is 1–100;

$R^3$ stands for a hydrogen atom, hydroxy, phenyl, straight-chain or branched $C_1$–$C_6$ alkyl, optionally substituted by hydroxy, or a group

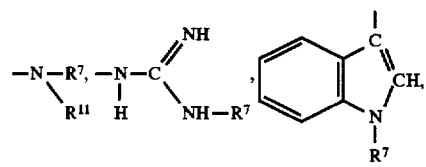

-continued

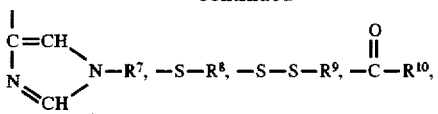

or

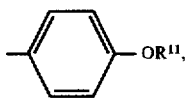

and $R^4$ stands for a hydrogen atom, $C_1$–$C_4$ alkyl or $C_1$–$C_8$ acyl optionally mono- or polysubstituted by hydroxy, or the group —$(CH_2)_n$—COOH or

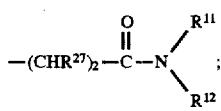

$R^3$ and $R^4$ alternatively can together with the nitrogen atom form a 5- or 6-membered ring, wherein each $R^3$ group can be the same or different and each $R^4$ group can be the same or different; and $R^6$ and $R_7$ independently stand for the group

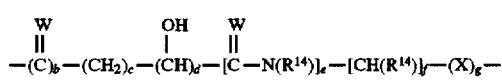

or the group

or the group

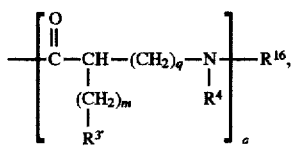

X stands for an oxygen or sulfur atom or the group

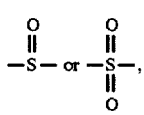

y stands for the group

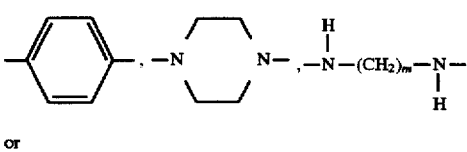

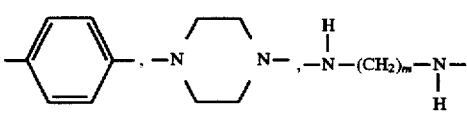

or

-continued

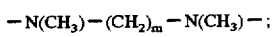

W stands for an oxygen or sulfur atom, $R^8$ stands for a hydrogen atom, $C_1$–$C_6$ alkyl or $C_1$–$C_{10}$ acyl.

$R^9$ means the group

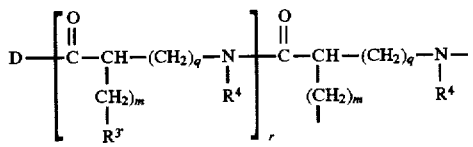

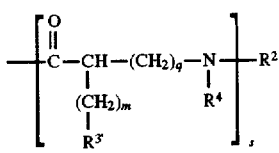

$R^{10}$ means hydroxy or the group

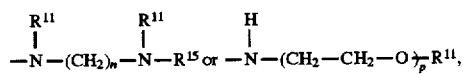

D means hydroxy or the group

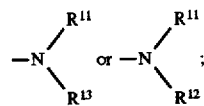

$R^{11}$ stands for a hydrogen atom, $C_1$–$C_4$ alkyl optionally mono- or polysubstituted by hydroxy, or the group —$(CH_2)_n$—COOH, $R^{12}$ stands for a hydrogen atom or hydroxy or the group

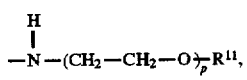

or an iodized benzene ring

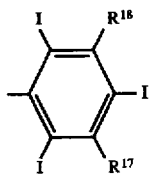

$R^{13}$ stands for the group

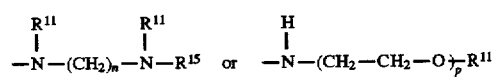

$R_{14}$ stands for a hydrogen atom, a carboxy group or a $C_1$–$C_{20}$ alkyl optionally interrupted one or more times by an oxygen atom and/or optionally mono- or polysubstituted by a hydroxy, carboxy, sulfono, phosphono and/or $C_1C_3$ alkoxy group, or the group

$R^{15}$ has the meaning mentioned under $R^6$ and $R^7$.

$R^{16}$ stands for the group

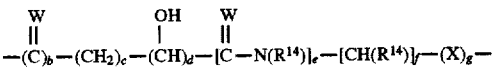

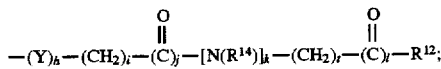

$R^{17}$ and $R^{18}$, respectively independently of one another, stand for a hydrogen atom or a group —$CONR^{20}R^{21}$ or —$NR^{22}COR^{23}$ $R^{19}$ means a $C_1$–$C_4$ alkyl optionally interrupted one or more times by an oxygen atom and/or optionally mono- or polysubstituted by a hydroxy, carboxy, sulfono, phosphono and/or $C_1$–$C_3$ alkoxy group, $R^{20}$ and $R^{21}$, independently of one another, stand for a hydrogen atom, a $C_1$–$C_{12}$ alkyl, $C_3$–$C_{12}$ cycloalkyl, $C_3$–$C_{12}$ cycloalkyl-$C_{1-12}$ alkyl or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a hydroxy, $C_1$–$C_3$ alkoxy, carboxy, sulfo and/or phosphono group, or $R^{20}$ and $R^{21}$ alternatively can together with the nitrogen atom form a 5- or 6-membered ring, which optionally can contain an oxygen atom or the group

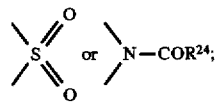

$R^{22}$ stands for a hydrogen atom or a $C_1$–$C_{12}$ alkyl, $C_3$–$C_{12}$ cycloalkyl, $C_3$–$C_{12}$ cycloalkyl-$C_{1-12}$ alkyl or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a carboxy, sulfono, phosphono group and/or hydroxy group, $R^{23}$ stands for a carboxy group or a straight chain or branched chain $C_1$–$C_{12}$ alkyl which is optionally interrupted one or more times by an oxygen atom, a carbonyl group and/or an imino group wherein the latter is optionally substituted by a carboxymethyl group, and/or the $C_{1-12}$-alkyl is optionally mono- or polysubstituted by a hydroxy, carboxy, sulfono, phosphono and/or $C_1$–$C_3$ alkoxy group, and $R^{24}$ stands for a carboxy group or a $C_1$–$C_{12}$ alkyl optionally interrupted one or more times by a carbonyl group and/or optionally mono- or polysubstituted by a hydroxy, $C_1$–$C_3$ alkoxy, carboxy, sulfono or phosphono group, $R^{27}$ stands for a hydrogen atom or $C_1$–$C_4$ alkyl, $R^{3'}$ stands for a hydrogen atom, hydroxy, phenyl, $NR_2^{11}$, straight-chain or branched alkyl optionally substituted by hydroxy, or $R^{3'}$ and $R^4$ can together with the nitrogen atom form a 5- or 6-membered ring, a in each case stands for 0–200, b, e, g, h, j, k and l are, in each case, the same or different and stand for 0 or 1, c and i are, in each case, the same or different and stand for 0 to 10, d, f, m, p, t and w are, in each case, the same or different and stand for 0 to 6, n stands for 0 to 20, and r and s are the same or different and stand for 0 to 100, wherein the total sum of all subscripts a, r, s and v is 10–200, and wherein at least 10 iodized benzene radicals are contained in the peptide;

or a salt thereof with physiologically acceptable organic bases, inorganic bases, amino acids and amino acid amides.

3. An iodine-containing peptide according to claim 1, wherein $R^1$ stands for hydroxy, $R^2$ stands for a dendrimere having $$\sum_{k=0}^{n-1} 2^k$$

reproduction units R, n represents the number of generations and is 1–100, q is 0–6, R is a radical of formula II

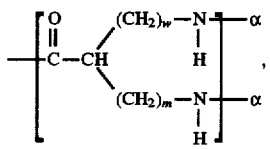

(II)

wherein

α for each generation up to n−1 is, in each case, a reproduction unit R, and for the nth generation is, in each case, the group

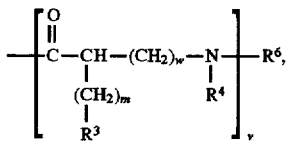

wherein v is 1–100, $R^3$ stands for a hydrogen atom, phenyl, straight-chain or branched $C_1$–$C_6$ alkyl or a group

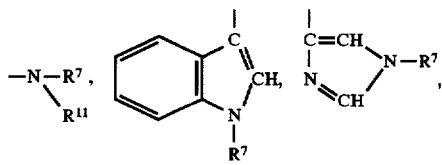

-continued

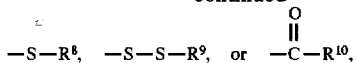

and $R_4$ stands for a hydrogen atom, methyl or ethyl, $R^3$ and $R^4$ alternatively can together with the nitrogen atom form a 5- or 6-membered ring, wherein each $R^3$ group can be the same or different and each $R^4$ group can be the same or different; and $R_6$ and $R^7$ stand for the group

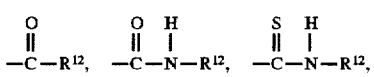

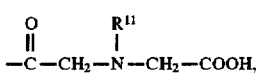

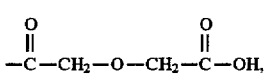

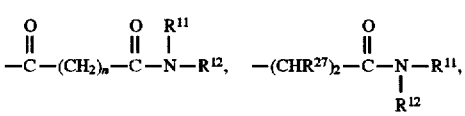

or

or the group

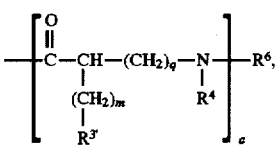

bound by the C-terminal end;

$R^8$ stands for a hydrogen atom or $C_1$–$C_6$ alkyl, $R^9$ means the group

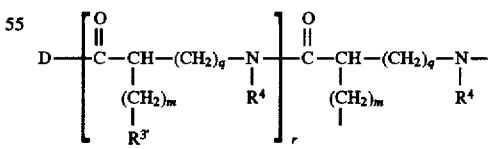

$R^{10}$ means hydroxy or the group

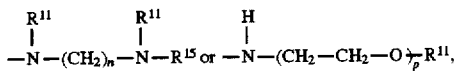

D means hydroxy or the group

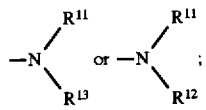

$R^{11}$ stands for a hydrogen atom. $C_1$–$C_4$ alkyl optionally mono- or polysubstituted by hydroxy, or the group —($CH_2$)—COOH.

$R^{12}$ stands for an iodized benzene ring

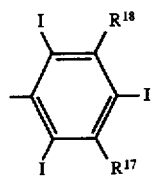

$R^{13}$ stands for the group

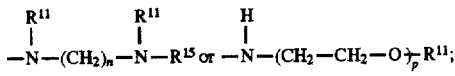

$R^{15}$ has the meaning indicated under $R^6$ and $R^7$, $R^{16}$ stands for the group

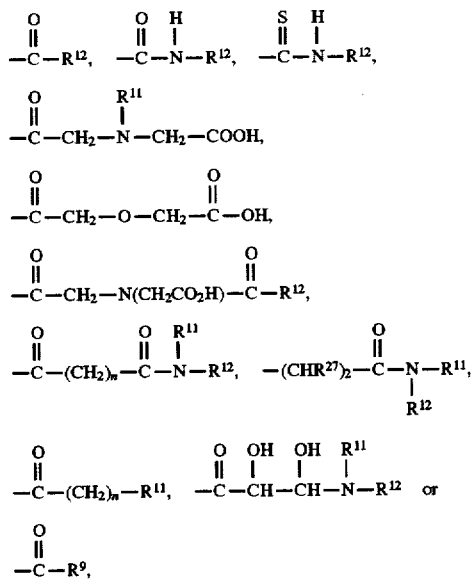

$R^{17}$ and $R^{18}$, respectively independently of one another, stand for a hydrogen atom or a group —$CONR^{20}R^{21}$ or —$NR^{22}COR^{23}$, $R^{20}$ and $R^{21}$, independently of one another, stand for a hydrogen atom, a $C_1$–$C_{12}$ alkyl, $C_3$–$C_{12}$ cycloalkyl, $C_3$–$C_{12}$ cycloalkyl-$C_{1-12}$ alkyl, or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a hydroxy, $C_1$–$C_3$ alkoxy, carboxy, sulfo and/or phosphono group, or $R^{20}$ and $R^{21}$ alternatively can together with the nitrogen atom form a 5- or 6-membered ring, which optionally can contain an oxygen atom or the group

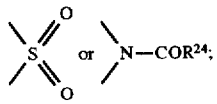

$R^{22}$ stands for a hydrogen atom or a $C_1$–$C_{12}$ alkyl, $C_3$–$C_{12}$ cycloalkyl, $C_3$–$C_{12}$ cycloalkyl-$C_{1-12}$ alkyl, or $C_3$–$C_{12}$ cycloalkyl substituted one or more times by $C_{1-12}$ alkyl, wherein in each case the alkyl and cycloalkyl groups can be optionally interrupted one or more times by a carbonyl group and/or optionally mono- or polysubstituted by a carboxy, sulfono, phosphono group and/or hydroxy group, $R^{23}$ stands for a carboxy group or a straight chain or branched chain $C_1$–$C_{12}$ alkyl which is optionally interrupted one or more times by an oxygen atom, a carbonyl group and/or an imino group wherein the latter is optionally substituted by a carboxymethyl group, and/or the $C_{1-12}$-alkyl is optionally mono- or polysubstituted by a hydroxy, carboxy, sulfono, phosphono and/or $C_1$–$C_3$ alkoxy group, and $R^{24}$ stands for a carboxy group or a $C_1$–$C_{12}$ alkyl optionally interrupted one or more times by a carbonyl group and/or optionally mono- or polysubstituted by a hydroxy, $C_1$–$C_3$ alkoxy, carboxy, sulfono or phosphono group, $R^{27}$ stands for a hydrogen atom or $C_1$–$C_4$ alkyl, $R^{3'}$ stands for a hydrogen atom, hydroxy, phenyl, $NR_2^{11}$, straight-chain or branched alkyl optionally substituted by hydroxy, or $R^{3'}$ and $R^4$ can together with the nitrogen atom form a 5- or 6-membered ring, a in each case stands for 0–200, m stands for 0 to 4, p is, in each case, the same or different and stands for 0 to 6, n stands for 0 to 20 and r and s are, in each case, the same or different and stand for 0 to 100, wherein the total sum of all subscripts a, r, s and v is 10–200,and wherein at least 10 iodized benzene radicals are contained in the peptide, or a salt thereof with physiologically acceptable organic bases, inorganic bases, amino acids and amino acid amides.

4. An iodine-containing peptide according to claim 1, wherein the total sum of all subscripts a, r, s and v is 20–80.

5. An iodine-containing peptide according to claim 2, wherein the total sum of all subscripts a, r, s and v is 20–80.

6. An iodine-containing peptide according to claim 3, wherein the total sum of all subscripts a, r, s and v is 20–80.

7. An iodine-containing peptide according to claim 1, wherein the total sum of all subscripts a, r, s and v is 30–60.

8. An iodine-containing peptide according to claim 2, wherein the total sum of all subscripts a, r, s and v is 30–60.

9. An iodine-containing peptide according to claim 3, wherein the total sum of all subscripts a, r, s and v is 30–60.

10. An iodine-containing peptide according to claim 1, wherein $R^5$ is a saccharide, oligosaccharide or polysaccharide.

11. An iodine-containing peptide according to claim 10, wherein $R^5$ is amylose or amylopectin.

12. An iodine-containing peptide according to claim 1, wherein said peptide contains 10–200 radicals of the subformula ![structure with benzene ring bearing three I atoms, $R^{18}$, $R^{17}$]

13. A process for the production of iodine-containing peptides of general formula I according to claim 1, said process comprising:

producing a peptide with free primary or secondary amino groups and the latter then are reacted with compounds of general formula III ![structure III: benzene ring with three I, G, $R^{18}$, $R^{17}$] (III)

in which $R^{17}$ and $R^{18}$ have the meanings indicated under general formula I and the carboxy and/or hydroxy groups contained in general formula II are present in protected form and G contains an activated group, which is able to react with the free amino group(s) of a peptide under conversion into linker E of the formula $$X_1-(C)_b-(CH_2)_c-(CH)_d-[\overset{W}{\overset{\|}{C}}-N(R^{14})]_e-[CH(R^{14})]_f-(X)_g-(Y)_h-(CH_2)_i-(\overset{O}{\overset{\|}{C}})_j-[N(R^{14})]_k-(CH_2)_r-(C)_l-X_2$$

$$\overset{OH}{\overset{|}{}}\quad \overset{W}{\overset{\|}{}} \quad \overset{O}{\overset{\|}{}}$$

in which W, X, Y, $R^{14}$, b, c, d, e, f, g, h, i, j, k, l and t have the meanings indicated under general formula I, $x_1$ is the binding position of the peptide, $x_2$ is the binding position of $R^{12}$, and finally, if in the peptide moiety free amino groups are still present, optionally these groups are reacted with compounds of general formula IV $$G-R^{28} \qquad (IV),$$

in which G has the meaning indicated under general formula II and $R^{28}$ stands for a hydrogen atom, hydroxy or the group $$-\overset{H}{\overset{|}{N}}-(CH_2-CH_2-O)_p-R^{11},$$

in which $R^{11}$ and p have the meanings indicated under general formula I, and the carboxy and hydroxy groups contained in general formula IV are present in protected form.

14. A pharmaceutical composition comprising at least one iodine-containing peptide according to claim 1, a physiologically acceptable medium, and optionally one or more galenic additives.

15. In a method of X-ray diagnosis comprising administering an X-ray contrast agent to a patient wherein the improvement is said agent contains at least one iodine-containing peptide according to claim 1.

16. In a method of X-ray diagnosis of vascular diseases comprising administering an X-ray contrast agent to a patient wherein the improvement is said agent contains at least one iodine-containing peptide according to claim 1.

17. A process according to claim 13, wherein said peptide with free primary or secondary amino groups is prepared by:

reacting solid phase peptide synthesis resin substituted with Fmoc-Ala, wherein Fmoc is fluorenylmethyloxycarbonyl and Ala is alanine, to remove Fmoc protecting groups;

suspending the deprotected resin and adding to the resultant suspension bis-Fmoc-lysine, benzatriazol-1-yl-oxytrispyrrolidinophosphonium hexafluorophosphate as coupling agent and 1-hydroxybenzotriazole as catalyst;

subjecting the resultant product to deprotection whereby Fmoc protection groups are removed;

repeating the suspension of the resin, addition of bis-Fmoc-lysine, benzotriazol-1-yl-oxy-trispyrrolidinophosphonium hexafluorophosphate and 1-hydroxybenzotriazole and deprotection a sufficient number of times to obtain the desired amplification;

thereafter suspending the resultant amplified resin with α-Fmoc-ε-BOC-lysine, wherein BOC is butoxycarbonyl, benzotriazol-1-yl-oxy-tris-pyrrolidinophosphonium hexafluorophosphate and 1-hydroxybenzotriazole; and subjecting the resultant product to deprotection for removal of Fmoc groups and repeating said suspending and deprotection to obtain a desired lysine chain length; and thereafter subjecting the resultant resin to a cleavage reaction to remove BOC protection groups.

18. An iodine-containing peptide according to claim 1, wherein said peptide has a molecular weight of 5,000–5,000,000.

19. An iodine-containing peptide according to claim 1, wherein said peptide has a molecular weight of 10,000–500,000.

20. An iodine-containing peptide according to claim 1, wherein said peptide has a molecular weight of 20,000–100,000.

21. An iodine-containing peptide according to claim 1, wherein said peptide is:

dotriacontakis-{3-(3-sodium carboxylatopropionylamino)-5-(2,3-dihydroxypropylcarbamoyl)-2, 4,6-triiodobenzoyl} derivative of the lysine-alanine copolymer ($K_3$) $_8K_4K_2K$—A—OH;

dotriacontakis-{3,5-di-(sodium carboxylatomethylcarbamoyl)-2,4,6-triiodophenylcarbamoyl} derivative of the lysine-alanine copolymer ($K_3$)$_8K_4K_2K$—A—OH;

dotriacontakis-{3-[(N-carboxymethyl)-sodium carboxylatomethyl-carbamoyl]-5-[N, N-bis-(sodium carboxylatomethyl)-carbamoyl]-2,4,6-triiodophenylcarbamoyl derivative of the lysine-alanine copolymer ($K_3$)$_8K_4K_2K$—A—OH;

octatetracontakis-{3-sodiumcarboxylatoformylamino-5-(2,3-dihydroxypropylcarbamoyl)-2, 4,6- triiodobenzoyl} derivative of the lysine-alanine copolymer $(K_5)_8K_4K_2K$—A—OH;

octatetracontakis-{3-(4-sodium carboxylato-3-oxabutyrylamino)-5-(2,3-dihydroxypropylcarbamoyl)-2,4,6-triiodobenzoyl} derivative of the lysine-alanine copolymer $(K_5)_8K_4K_2K$—A—OH;

octatetracontakis-{3-[N,N-bis-(sodiumcarboxylatomethyl)-carbamoyl)]-5-methoxyacetylamino-2,4,6-triiodobenzoyl} derivative of the lysine-alanine copolymer $(K_5)_8K_4K_2K$—A—OH;

octatetracontakis-{N-|3,5-di-(acetylamino)-2,4,6-triiodobenzoyl]-N-(sodium carboxylatomethyl)-glycyl derivative of the lysine-alanine copolymer $(K_5)_8K_4K_2K$—A—OH;

octaoctakis- {3 -[(N-sodium carboxylatomethyl)-methoxyacetylamino-5-(2,3 -dihydroxy-propylcarbamoyl)-2, 4,6-triiodobenzoyl} derivative of the lysine-alanine copolymer $(K_{10})_8K_4K_2K$—A—OH;

dotetracontakis-{3,5-[N,N-bis-(sodium carboxylatomethyl)-carbamoyl)]-2,4,6-triiodophenylthiocarbamoyl} derivative of the lysine-alanine copolymer $(K_{20})_2K$—A—OH;

dotetracontakis-{3-sodium carboxylatomethylcarbamoyl-5-[(N-methoxyacetyl)methylamino]-2, 4,6-triiodobenzoyl derivative of the lysine-alanine copolymer $(K_{20})_2K$—A—OH;

octatetracontakis-{N-methoxyacetyl-3-methylamino-5-(2-sodiumsulfonatoethylcarbamoyl)-2, 4,6-triiodobenzoyl} derivative of the lysine-alanine copolymer $(K_5)_8K_4K_2K$—A—OH;

dotriacontakis-{3,5-bis-(disodium phosphonatomethylcarbamoyl)-2,4,6-triiodarylcarbamoyl} derivative of the lysine-alanine copolymer $(K_3)_8K_4K_2K$—A—OH;

dotriacontakis-{3-(3-sodium carboxylatopropionylamino)-5-(2,3-dihydroxypropylcarbamoyl)-2, 4,6-triiodobenzoyl} derivative of the lysine-proline-cysteine-alanine copolymer $(_{K3})_8K_4K_2K-P_{10}$-C-A; or octatriacontakis-{3-(4-sodium carboxylato-3-oxabutyrylamino)-5-(2,3 -dihydroxypropylcarbamoyl)-2, 4,6-triiodobenzoyl}-tetrakis-(4-sodium carboxylato-3-oxabutyryl) derivative of the lysine-alanine copolymer $(K_{20})_2K$—A—OH;

wherein K is lysine and A is alanine.

22. An iodine-containing peptide according to claim 1, wherein $R^{20}$, $R_{20}$ and $R^{22}$ are, in each case independently, H, methyl, hydroxymethyl, ethyl, 2-hydroxyethyl, 2-hydroxy-1-(hydroxymethyl)-ethyl, 1-(hydroxymethyl)-ethyl, propyl, isopropyl, 2-hydroxypropyl, 3-hydroxypropyl, 2,3-dihydroxypropyl, 1,2,3-trihydroxypropyl, butyl, isobutyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl, 1,2,4-trihydroxybutyl, pentyl, cyclopentyl, cyclohexyl, 2,3,4,5,6-pentahydroxyhexyl, 2-methoxyethyl, carboxymethyl, 2-sulfoethyl, phosphonomethyl, 2-carboxyethyl, 10-hydroxydecyl, carboxy, 3-sulfopropyl, or 2-phosphonoethyl.

23. An iodine-containing peptide according to claim 1, wherein $R^{23}$ is methyl, hydroxymethyl, ethyl, 2-hydroxyethyl, 2-hydroxy-1-(hydroxymethyl)-ethyl, 1-(hydroxymethyl)-ethyl, propyl, isopropyl, 2-hydroxypropyl, 3-hydroxypropyl, 2,3-dihydroxypropyl, 1,2,3-trihydroxypropyl, butyl, isobutyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl, 1,2,4-trihydroxybutyl, pentyl, cyclopentyl, cyclohexyl, 2,3,4,5,6-pentahydroxyhexyl, 2-methoxyethyl, carboxymethyl, 2-sulfoethyl, phosphonomethyl, 2-carboxyethyl, 10-hydroxydecyl, carboxy, 3-sulfopropyl, or 2-phosphonoethyl.

24. An iodine-containing peptide according to claim 1, wherein $R^4$, $R^{11}$ and $R^{19}$, in each case independently, are methyl, ethyl, propyl, butyl, isobutyl, hydroxymethyl, 2-hydroxyethyl, 2-hydroxy-1-(hydroxymethyl)-ethyl, 1-(hydroxymethyl)-ethyl, 2-hydroxypropyl, 3-hydroxypropyl, 2,3-dihydroxypropyl, 1,2,3-trihydroxypropyl, butyl, isobutyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl or 1,2,4-trihydroxybutyl.

25. An iodine-containing peptide according to claim 1, wherein $R^{27}$ is methyl, ethyl, propyl, butyl or isobutyl.

26. An iodine-containing peptide according to claim 1, wherein $R^8$ is methyl, ethyl, propyl, butyl, isobutyl, pentyl or hexyl.

27. An iodine-containing peptide according to claim 1, wherein $R^3$ is methyl, ethyl, propyl, butyl, isobutyl, hydroxymethyl, 2-hydroxyethyl, 2-hydroxy-1-(hydroxymethyl)-ethyl, 1-(hydroxymethyl)-ethyl, 2-hydroxypropyl, 3-hydroxypropyl, 2,3-dihydroxypropyl, 1,2,3-trihydroxypropyl, butyl, isobutyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl, 1,2,4-trihydroxybutyl or 2,3,4,5,6-pentahydroxyhexyl.

28. An iodine-containing peptide according to claim 1, wherein n is 1–5 and v is 1–20.

* * * * *